US012599720B2

(12) United States Patent
Abal et al.

(10) Patent No.: US 12,599,720 B2
(45) Date of Patent: Apr. 14, 2026

(54) REAL TIME DETECTION AND MONITORING OF FLUID VOLUME AND FLOW RATE

(71) Applicant: CareFusion 303, Inc., San Diego, CA (US)

(72) Inventors: Daniel M. Abal, San Diego, CA (US); Brendan John Burgess, Poway, CA (US); Ramkumar Subramanian, San Diego, CA (US); Reza Paiam, San Diego, CA (US); Ronald Hidalgo, Killaloe (IE); Hermogenes Escala, Limerick City (IE); James Hennessy, Annacotty (IE)

(73) Assignee: CAREFUSION 303, INC., San Diego, CA (US)

( * ) Notice: Subject to any disclaimer, the term of this patent is extended or adjusted under 35 U.S.C. 154(b) by 859 days.

(21) Appl. No.: 17/511,449

(22) Filed: Oct. 26, 2021

(65) Prior Publication Data

US 2022/0126020 A1     Apr. 28, 2022

Related U.S. Application Data

(60) Provisional application No. 63/105,800, filed on Oct. 26, 2020.

(51) Int. Cl.
*A61M 5/168* (2006.01)
*A61M 5/14* (2006.01)
*A61M 5/142* (2006.01)

(52) U.S. Cl.
CPC ...... *A61M 5/16895* (2013.01); *A61M 5/1415* (2013.01); *A61M 5/142* (2013.01);
(Continued)

(58) Field of Classification Search
CPC ............ A61M 5/16895; A61M 5/1415; A61M 5/142; A61M 5/16831;
(Continued)

(56) References Cited

U.S. PATENT DOCUMENTS

| | | | | |
|---|---|---|---|---|
| 3,690,318 | A | * | 9/1972 | Gorsuch ........... A61M 5/16845 |
| | | | | 222/25 |
| 3,884,228 | A | * | 5/1975 | Hahn .................. A61M 5/1689 |
| | | | | 604/245 |

(Continued)

FOREIGN PATENT DOCUMENTS

| | | | | | |
|---|---|---|---|---|---|
| CN | 106139319 | A | * | 11/2016 | .......... A61M 5/1684 |
| CN | 108283741 | A | * | 7/2018 | ........ A61M 5/16831 |

(Continued)

OTHER PUBLICATIONS

CN106139319 English translation (Year: 2016).*

(Continued)

*Primary Examiner* — Nathan R Price
(74) *Attorney, Agent, or Firm* — MASCHOFF BRENNAN

(57) ABSTRACT

A method of detecting a fault condition in an infusion process, the method includes receiving a programmed flow rate pertaining to a fluid infusion provided by an infusion device; determining, a first weight of an infusion container associated with the fluid infusion provided by the infusion device at a first time; determining a second weight of the infusion container at a second time; determining based on the first weight and the second weight, a determined flow rate of the fluid infusion provided by the infusion device between the first time and the second time. The method includes determining a difference between the determined flow rate and the programmed flow rate. When a magnitude of the difference between the determined flow rate and the programmed flow rate satisfies a predetermined threshold, (Continued)

by the processor: causing an output of the infusion device or the weight sensor to indicate the fault condition.

17 Claims, 15 Drawing Sheets

(52) U.S. Cl.
CPC .... *A61M 5/16818* (2013.01); *A61M 5/16831* (2013.01); *A61M 5/16845* (2013.01); *A61M 2005/14208* (2013.01); *A61M 2205/3334* (2013.01); *A61M 2205/3393* (2013.01); *A61M 2205/50* (2013.01)

(58) Field of Classification Search
CPC .......... A61M 2005/14208; A61M 2205/3393; A61M 2205/3334; A61M 2205/50; A61M 5/16818; A61M 5/16845; A61M 5/00; A61M 5/16827
See application file for complete search history.

(56) References Cited

U.S. PATENT DOCUMENTS

| | | | | |
|---|---|---|---|---|
| 4,457,750 | A * | 7/1984 | Hill | A61M 5/16895 128/DIG. 13 |
| 4,650,464 | A * | 3/1987 | Ruiz | A61M 5/16845 128/DIG. 13 |
| 4,670,007 | A * | 6/1987 | Wheeldon | A61M 5/172 128/DIG. 13 |
| 5,040,699 | A * | 8/1991 | Gangemi | G01G 19/346 141/105 |
| 5,056,568 | A * | 10/1991 | DiGianfilippo | B29C 53/083 141/83 |
| 5,112,019 | A * | 5/1992 | Metzler | A61M 3/0266 248/176.1 |
| 5,791,881 | A * | 8/1998 | Moubayed | F04B 43/082 417/474 |
| 6,284,142 | B1 * | 9/2001 | Muller | A61M 1/362261 604/4.01 |
| 8,230,877 | B2 * | 7/2012 | Roberge | G05D 7/0635 137/488 |
| 9,726,167 | B2 * | 8/2017 | Schweitzer | A61M 5/365 |
| 10,576,202 | B2 | 3/2020 | Sims et al. | |
| 11,839,737 | B2 * | 12/2023 | Frausto | A61M 5/16845 |
| 12,201,806 | B2 * | 1/2025 | Frausto | A61M 5/1415 |
| 2003/0106969 | A1 * | 6/2003 | Dillon | A61M 5/1415 248/129 |
| 2004/0116846 | A1 | 6/2004 | Olivera et al. | |
| 2011/0205074 | A1 * | 8/2011 | Feng | A61M 5/16845 340/613 |
| 2013/0150821 | A1 * | 6/2013 | Bollish | A61M 5/16895 422/44 |
| 2013/0336814 | A1 * | 12/2013 | Kamen | A61M 5/16859 417/302 |
| 2014/0074008 | A1 | 3/2014 | Fontanazzi et al. | |
| 2014/0088483 | A1 | 3/2014 | Fontanazzi et al. | |
| 2014/0228755 | A1 * | 8/2014 | Darrah | A61M 5/445 604/113 |
| 2015/0051573 | A1 * | 2/2015 | Tieck | A61M 5/16831 604/67 |
| 2015/0126959 | A1 * | 5/2015 | Nakash | A61M 5/1407 604/153 |
| 2016/0228639 | A1 * | 8/2016 | Zin | A61M 5/16813 |
| 2017/0203035 | A1 | 7/2017 | Freudenthal | |
| 2018/0177945 | A1 * | 6/2018 | Sims | G16H 20/17 |
| 2018/0353680 | A1 * | 12/2018 | Al Hatib | A61M 5/172 |
| 2019/0015589 | A1 | 1/2019 | Shtram et al. | |
| 2020/0360604 | A1 | 11/2020 | Kolko et al. | |
| 2021/0369961 | A1 * | 12/2021 | Hassani | A61M 39/24 |

FOREIGN PATENT DOCUMENTS

| | | | | |
|---|---|---|---|---|
| CN | 104800911 | B | 9/2018 | |
| CN | 109331245 | A | 2/2019 | |
| CN | 211327337 | U | 8/2020 | |
| CN | 115429966 | A * | 12/2022 | A61M 5/1415 |
| CN | 116570793 | A * | 8/2023 | A61M 5/1415 |
| CN | 116650758 | A * | 8/2023 | A61M 5/16818 |
| DE | 1616205 | A1 * | 1/1971 | A61M 5/16818 |
| DE | 202015103317 | U1 * | 9/2015 | A61M 1/02 |
| FR | 2458289 | A1 * | 1/1981 | G05D 7/0635 |
| KR | 20170120774 | A * | 11/2017 | A61M 5/16818 |
| WO | WO-2009005950 | A2 * | 1/2009 | A61B 5/002 |
| WO | WO-2011017215 | A1 * | 2/2011 | A61J 1/05 |
| WO | WO-2019195568 | A2 * | 10/2019 | A61M 1/28 |
| WO | WO-2024151261 | A1 * | 7/2024 | A61M 5/1415 |

OTHER PUBLICATIONS

CN108283741 English translation (Year: 2018).*
CN115429966 English translation (Year: 2022).*
CN116570793 English translation (Year: 2023).*
CN116650758 English translation (Year: 2023).*
DE202015103317 English translation (Year: 2015).*
FR2458289 English translation (Year: 1981).*
KR20170120774 English translation (Year: 2017).*
DE1616205 English translation (Year: 1971).*
European Office Action for Application No. 21811594.7, dated Mar. 21, 2025, 6 pages.
Chinese Office Action for Application No. 202180087546.3, dated Jul. 22, 2025, 18 pages including translation.
Chinese Office Action for Application No. 202180087546.3, dated Feb. 14, 2026, 16 pages including translation.

* cited by examiner

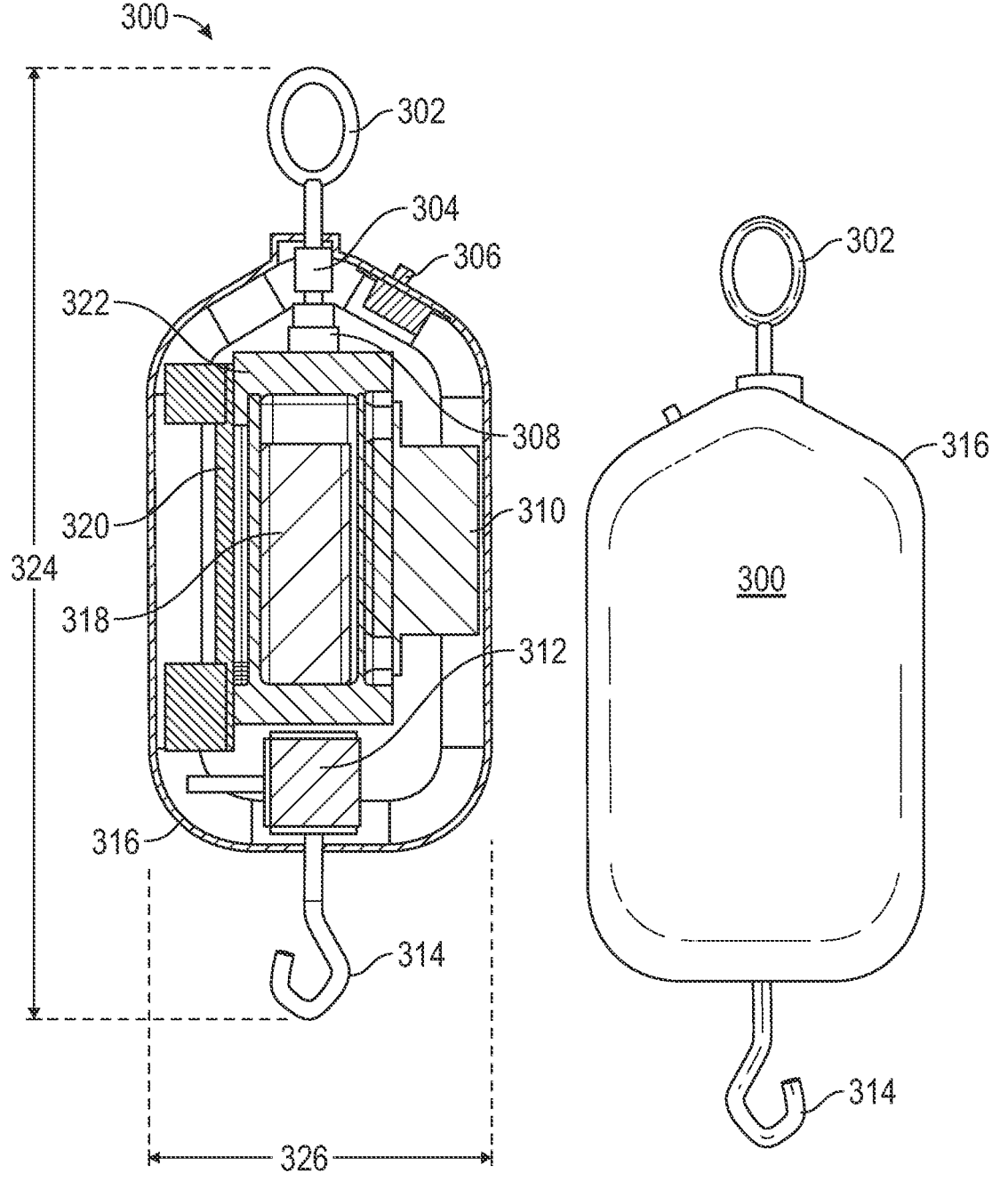
FIG. 3A                    FIG. 3B

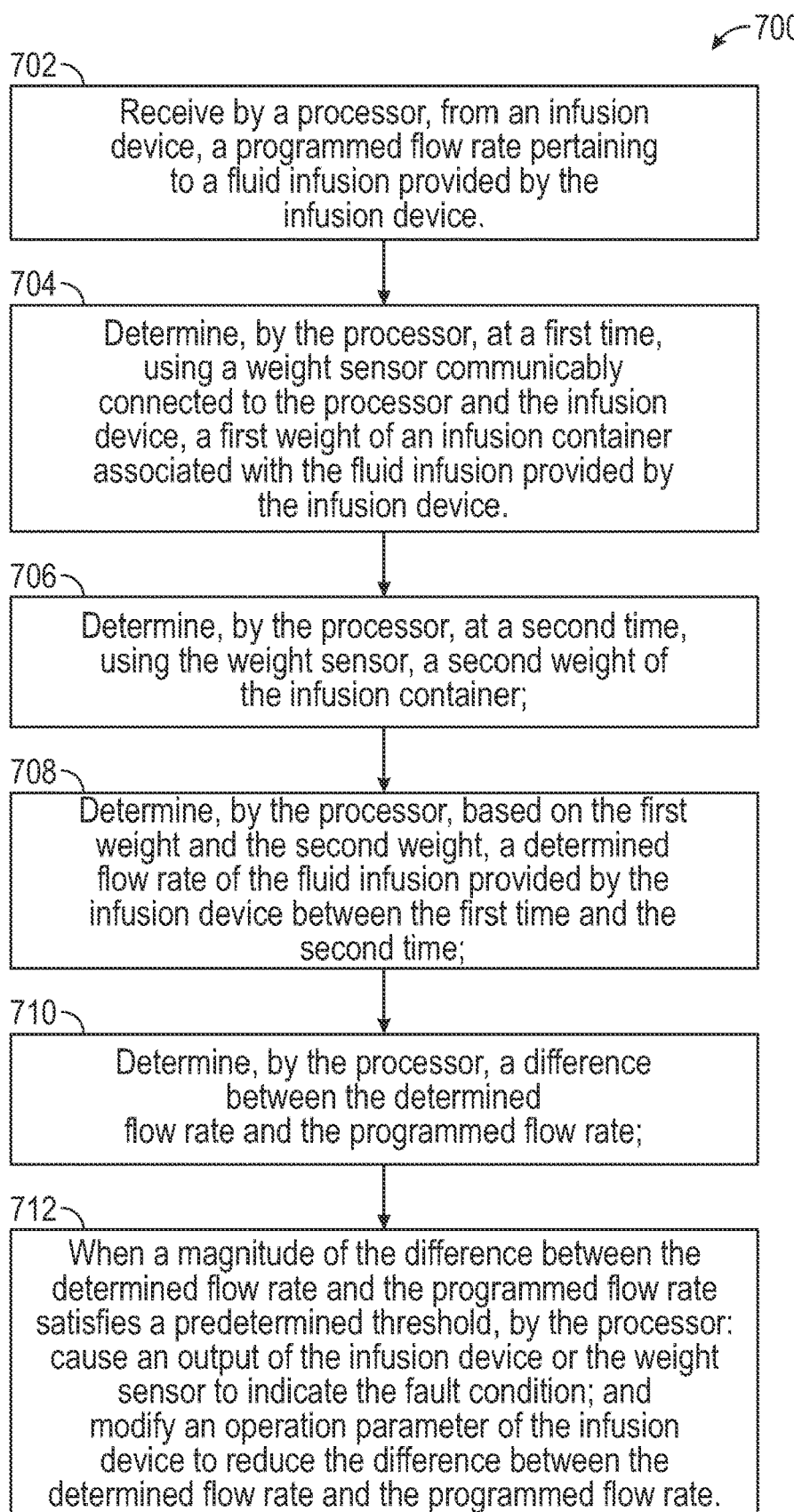

702
Receive by a processor, from an infusion device, a programmed flow rate pertaining to a fluid infusion provided by the infusion device.

704
Determine, by the processor, at a first time, using a weight sensor communicably connected to the processor and the infusion device, a first weight of an infusion container associated with the fluid infusion provided by the infusion device.

706
Determine, by the processor, at a second time, using the weight sensor, a second weight of the infusion container;

708
Determine, by the processor, based on the first weight and the second weight, a determined flow rate of the fluid infusion provided by the infusion device between the first time and the second time;

710
Determine, by the processor, a difference between the determined flow rate and the programmed flow rate;

712
When a magnitude of the difference between the determined flow rate and the programmed flow rate satisfies a predetermined threshold, by the processor: cause an output of the infusion device or the weight sensor to indicate the fault condition; and modify an operation parameter of the infusion device to reduce the difference between the determined flow rate and the programmed flow rate.

FIG. 7

| Fault Condition | Flow Rate (mL/hr) | % Flow Rate Error | | Result |
| --- | --- | --- | --- | --- |
| | | IV Bag Load Cell | Lab Scale | |
| 2 Bosses | 1 | 3.9 | -11.2 | 0 |
| 1 Boss | 1 | -110.7 | -15.0 | 2 |
| 5 Bosses | 1 | -71.4 | -17.8 | 2 |
| 3 Bosses | 1 | 1094.3 | 1052.0 | 0 |
| Leaking Occluders | 1 | 653.0 | 107.0 | 0 |
| 2 Bosses | 10 | -22.9 | -12.8 | 2 |
| 1 Boss | 10 | -17.2 | -15.0 | 0 |
| 5 Bosses | 10 | -21.4 | -17.7 | 2 |
| 3 Bosses | 10 | 251.6 | 258.4 | 0 |
| Leaking Occluders | 10 | 42.0 | 33.1 | 0 |
| 2 Bosses | 25 | -10.6 | -10.0 | 0 |
| 1 Boss | 25 | 17.9 | -15.4 | 0 |
| 5 Bosses | 25 | -12.9 | -18.1 | 0 |
| 3 Bosses | 25 | 7.0 | 6.7 | 0 |
| Leaking Occluders | 25 | 258.3 | 63.5 | 0 |
| 2 Bosses | 100 | -13.6 | -13.0 | 0 |
| 1 Boss | 100 | -13.3 | -13.2 | 0 |
| 5 Bosses | 100 | -17.7 | -17.9 | 0 |
| 3 Bosses | 100 | -17.0 | -17.7 | 0 |
| Leaking Occluders | 100 | 59.0 | 60.3 | 0 |

| | | | |
| --- | --- | --- | --- |
| No of Tests | 20 | | |
| Type 1 Error | 0 | 0% | |
| Type 2 Error | 40 | 20% | |

FIG. 9

REAL TIME DETECTION AND MONITORING OF FLUID VOLUME AND FLOW RATE

CROSS REFERENCE TO RELATED APPLICATIONS

This application claims the benefit of U.S. Provisional Application Ser. No. 63/105,800, entitled "REAL TIME DETECTION AND MONITORING OF FLUID VOLUME AND FLOW RATE," filed on Oct. 26, 2020, the entirety of which is incorporated herein by reference.

TECHNICAL FIELD

This application relates generally to detecting flow rate and monitoring intravenous (IV) bag volume in infusion processes.

BACKGROUND

Medical devices such as infusion devices are used to infuse medical fluids to patients. Uncontrolled flow may occur when the infusion device delivers a fluid flow that is outside the tolerances for a flow rate accuracy, or a volume delivered, or exceeds a critical volume defined for a particular infusion device.

SUMMARY

Accordingly, there is a need for devices and methods that help improve patient safety by monitoring and detecting uncontrolled flows in an infusion process, and alerting a care provider to correct the fault condition as quickly as possible.

One method to verify the flow rate and volume delivered to a patient is to measure the volume of fluid that is consumed by the infusion pump. This is done, for example, by using a system that monitors the weight of the IV container that provides the fluid to the pump. The system measures a weight of an IV container over an infusion period and determines a rate of consumption of the volume of infusion fluids in the IV container by the decrease in weight over time. The determined rate of consumption is then compared to an expected flow rate that is programmed to be delivered by the infusion pump. The system can issue an alarm to notify a caregiver when a discrepancy in the expected flow is caused by a failure in the system.

An IV container hanger which integrates a sensor measures the fluid weight in the container. The change in weight over time is converted to the volume flow rate by the fluid density. The hanger also incorporates a sensor conditioning circuit, wireless communication circuitry, a power supply, and firmware to perform the flow rate calculation. Information is transmitted wirelessly between the infusion device and the hanger. Data such as the fluid density, can be obtained from a library database (e.g., Alaris Guardrails™ Library). The programmed flow rate, and the start of the infusion, is transmitted between the hanger and infusion device. Firmware in the hanger uses the weight depletion data to calculate flow rate and uses criteria to determine a fault condition. Any deviation from the criteria is identified as a fault condition, and is relayed to the infusion device alarm system to alert the clinician and or stop the pump until the condition is corrected.

The system has the ability to detect abnormal conditions such as faults in the pumping system that cause excessive flow or unusual flow conditions. Infusion flow rates can range from a low of 0.1 mL/hr, to a maximum of 1200 mL/hr. It is desirable that a fault condition can be detected very quickly to ensure that the patient is not harmed by excessive administration of critical medications. During low flow rates (e.g., below 1 mL/hr), an algorithm is used to analyze the flow during a filling portion of the pumping cycle to ensure that it is performing as expected, so that the system would provide an earlier indication of an unusual condition.

The disclosed devices and methods can work with any type and size of IV container, and can be used to identify a deviation from the programmed flow rate, and provide an alarm when an IV container is empty. When two hangers are used with primary and secondary IV bags, the system can monitor sympathetic flow and secondary clamp closure. The disclosed devices and methods can provide a tracking record of the medication volume infused to a patient, and may also be able to detect incorrect line connected to pump.

The disclosed subject matter also relates to a method of detecting a fault condition in an infusion process includes receiving, by a processor, from an infusion device, a programmed flow rate pertaining to a fluid infusion provided by the infusion device. The method includes determining, by the processor, at a first time, using a weight sensor communicably connected to the processor and the infusion device, a first weight of an infusion container associated with the fluid infusion provided by the infusion device. The method includes determining, by the processor, at a second time (e.g., at a predetermined period of time after the first time), using the weight sensor, a second weight of the infusion container. The method includes determining, by the processor, based on the first weight and the second weight, a determined flow rate of the fluid infusion provided by the infusion device between the first time and the second time. The method includes determining, by the processor, a difference between the determined flow rate and the programmed flow rate. When a magnitude of the difference between the determined flow rate and the programmed flow rate satisfies a predetermined threshold, causing an output of the infusion device or the weight sensor to indicate the fault condition; and modifying an operation parameter of the infusion device to reduce the difference between the determined flow rate and the programmed flow rate. The method may be implemented using a system that includes one or more processors and a memory including instructions that, when executed by the one or more processors, cause the one or more processors to perform the steps of the method described herein.

Other aspects include corresponding apparatus, and computer program products for implementation of the corresponding system and its features.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description below, in conjunction with the following drawings. Like reference numerals refer to corresponding parts throughout the figures and description.

FIG. 3A depicts an example device for determining a fault condition in an infusion process, according to aspects of the subject technology.

FIG. 3B depicts an external view of an example device shown in FIG. 3A.

FIG. 7 depicts an example method for determining a fault condition during an infusion process, according to aspects of the subject technology.

FIG. 9 tabulates some example testing data from an example system implemented according to aspects of the subject technology.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Figure 1:
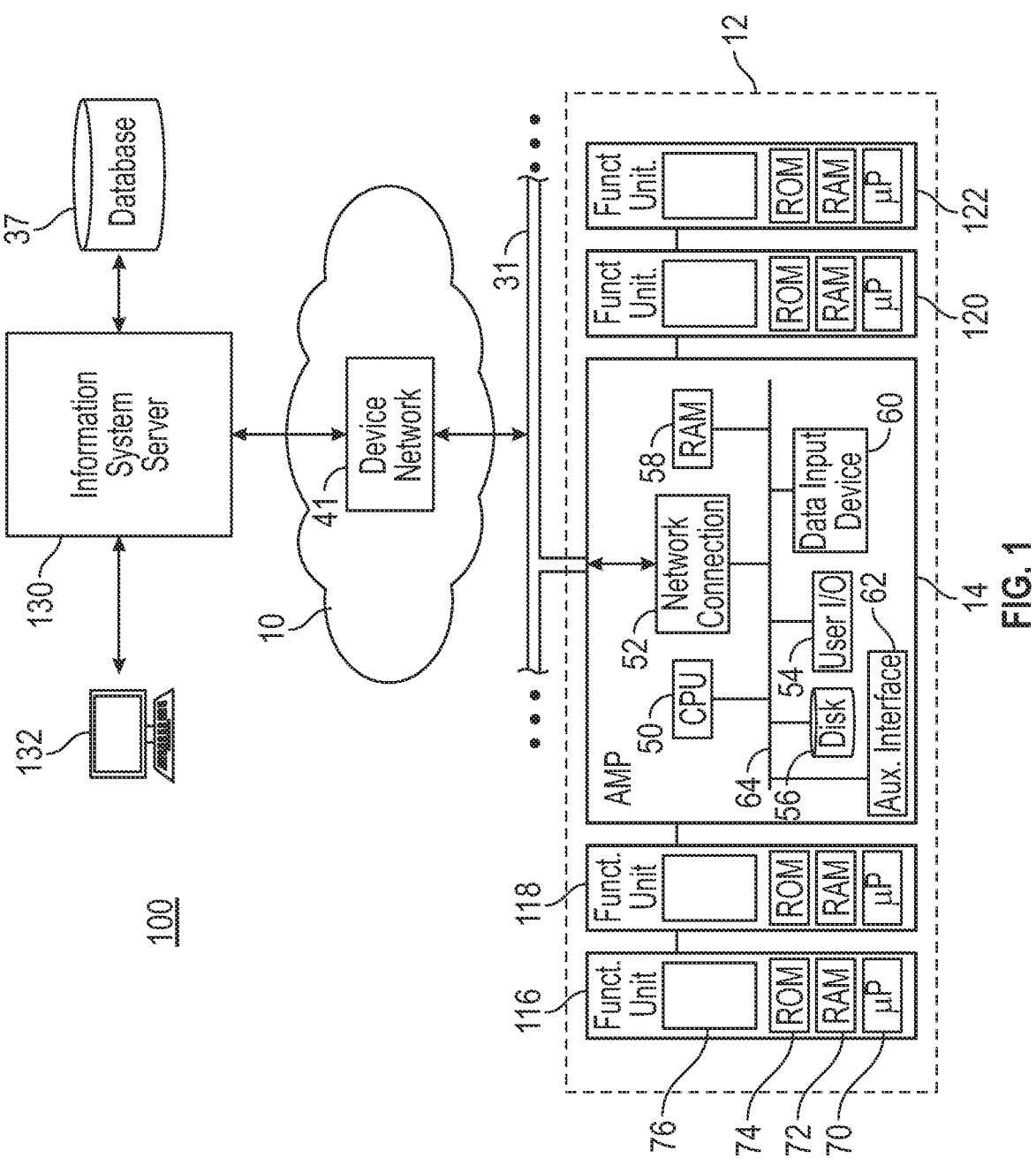
FIG. 1 depicts an example of an institutional patient care system of a healthcare organization, according to aspects of the subject technology.

FIG. 1 depicts an example of an institutional patient care system 100 of a healthcare organization, according to aspects of the subject technology. In FIG. 1, a patient care device (or "medical device" generally) 12 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each patient care device 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 41 by which patient care devices 12 (and other devices) communicate in accordance with normal operations.

Additionally, institutional patient care system 100 may incorporate a separate information system server 130, the function of which will be described in more detail below. Moreover, although the information system server 130 is shown as a separate server, the functions and programming of the information system server 130 may be incorporated into another computer, if such is desired by engineers designing the institution's information system. Institutional patient care system 100 may further include one or multiple device terminals 132 for connecting and communicating with information system server 130. Device terminals 132 may include personal computers, personal data assistances, mobile devices such as laptops, tablet computers, augmented reality devices, or smartphones, configured with software for communications with information system server 130 via network 10.

Patient care device 12 comprises a system for providing patient care, such as that described in Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 116, 118, 120, 122. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 116, 118, 120 and 122, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 116, 118, 120, 122 are any devices for providing care to a patient or for monitoring patient condition. As shown in FIG. 1, at least one of functional modules 116, 118, 120, 122 may be an infusion pump module such as an intravenous infusion pump for delivering medication or other fluid to a patient. For the purposes of this discussion, functional module 116 is an infusion pump module. Each of functional modules 118, 120, 122 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 118, 120 and/or 122 may be a printer, scanner, bar code reader or any other peripheral input, output or input/output device.

Each functional module 116, 118, 120, 122 communicates directly or indirectly with interface unit 14, with interface unit 14 providing overall monitoring and control of device 12. Functional modules 116, 118, 120, 122 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 116, 118, 120, 122 may include module-specific components 76, a microprocessor 70, a volatile memory 72 and a nonvolatile memory 74 for storing information. It should be noted that while four functional modules are shown in FIG. 1, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 116.

While each functional module may be capable of a least some level of independent operation, interface unit 14 monitors and controls overall operation of device 12. For example, as will be described in more detail below, interface unit 14 provides programming instructions to the functional modules 116, 118, 120, 122 and monitors the status of each module. The programming instructions may be based a volume or flow rate detected using at least some of the features described.

Patient care device 12 is capable of operating in several different modes, or personalities, with each personality defined by a configuration database. The configuration database may be a database 56 internal to patient care device, or an external database 37. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in health information server (HIS) 30, decision support 48, remote data server 49, hospital department or unit stations 46, or within patient care device 12 itself.

Direct communications with medical devices operating on a network in accordance with the subject technology may be performed through information system server 30, also known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Flow rate refers to the volume of fluid that is displaced over time, and can be either instantaneous flow or cumulative flow. Instantaneous flow is the volume of flow over a fixed period of time. Cumulative flow is the cumulative value of flow from the start to the finish of the measurement. For example, a 500 mL of medication infused over a period of 8 hour, represents a cumulative flow rate of (500 mL/8 hour) 62.5 mL/hr. Flow rate accuracy performance is typically described by trumpet curves which display the flow continuity for both the instantaneous and cumulative flow rates.

The pump flow rate depends on factors such as tubing dimensions (e.g., inner diameter, length, material properties), mechanism speed (e.g., cam rotations per minute (RPM)), and tubing occlusion which is the amount of squeeze applied to the tubing to create a fluid seal. The pump flow rate is also dependent on the tubing wall thickness and occluder finger force. Nonconformance in any of these or other fault conditions can result in uncontrolled flow rate or volume delivered by the pump. Thus, there is a need to be able to verify the flow rate and volume delivered by the pump, present a notification of any aberrant condition, and, if possible, adjust one or more medical devices to ensure and enhance patient safety.

Figure 2:
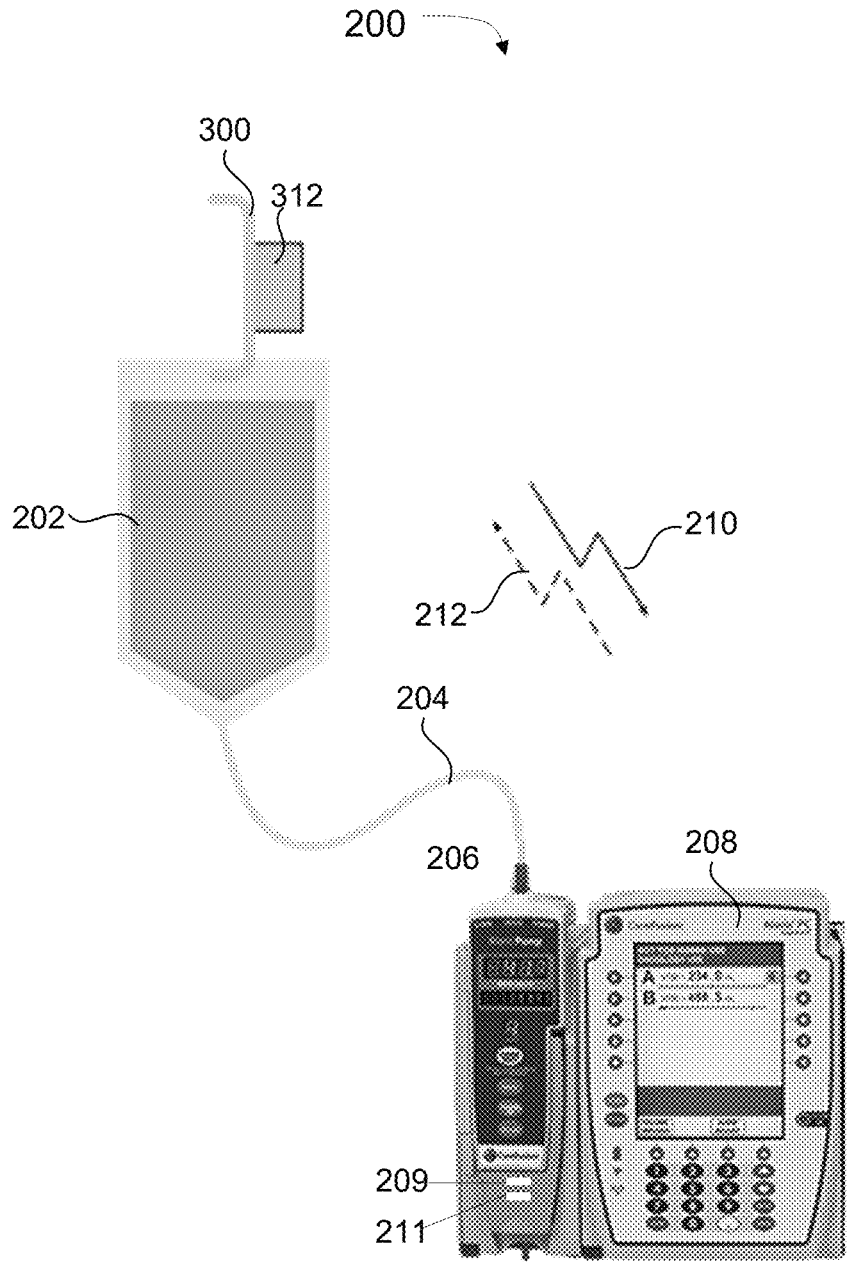
FIG. 2 depicts an example of a system for determining a fault condition in an infusion process, according to aspects of the subject technology.

FIG. 2 shows a system 200 for determining a fault condition in an infusion process, according to aspects of the subject technology. The system 200 incorporates a sensor (e.g., a load cell 312) in a hanger 300 that measures the weight of an IV container 202 that is hanging from the sensor. IV containers are typically hung from IV poles or other fixture proximate to the infusion pump at a specific head height to afford an appropriate gravitational pull on the fluid (e.g., fluid pressure) for the infusion. The sensor in the hanger 300 interfaces between the hanging fixture and the IV container 202 to measure the weight of the IV container 202. The weight is converted to fluid volume using the known density of the fluid inside the IV container 202.

Clause 201.12.1.102 of IEC 60601-2-24:2012 prescribes test requirements for manufacturers to follow when determining an accuracy of an infusion pump. For example, a manufacturer specifies the parameters and configurations of a test set-up to determine the accuracy of the pump in delivering medication. The setup described in the test requirements may not match the setup in a real patient setting. Thus, the accuracy of infusion in a real patient setting may deviate from the results from standard test setup, and over-infusion and/or under-infusion may occur.

An end-user selects a flow rate and/or VTBI (volume to be infused). The flow rate is typically measured in ml/hr and the VTBI is typically measured in ml. By using these two known inputs, the pump calculates a total duration for completing the infusion.

$$\text{Duration} = \frac{VTBI}{\text{Flow Rate}}$$

In some implementations, the end-user also selects a medication type. The selection of the medication type, the flow rate, and the VTBI can be replaced by auto-population (e.g., by scanning a barcode on the medication using a barcode reader).

To calculate if the required Duration is already met, The infusion pump receives feedback from an encoder wheel which is attached to the pumping motor in the infusion pump to determine if time lapsed since beginning of the infusion has exceeded the duration calculated based on VTBI and the flow rate. For example, a "number of encoders" is calculated by multiplying the motor speed, with the number of encoder per revolution of the encode wheel, and the duration (e.g., time elapsed since the start of the infusion process), as shown in the equation below. Therefore, if the pump completes the number of encoders at the pre-determined motor speed, the infusion pump is able to estimate if the infusion is completed.

Number of Encoders=(Motor Speed)×(Encoder per Revolution)×(Duration)

The estimation of the volume infused as described above is a simplified explanation. The pre-determined motor speed maybe identified by calibration at relevant points within a flow rate range defined by the manufacturer of the infusion pump. A correction coefficient in the calculation may also be introduced to compensate for factors that may contribute to deviations from the calculation described above. Without additional capacities (e.g., to check a weight of the medication or IV bag), the infusion pump may incorrectly determine that VTBI is completed using feedback only from the motor encoder.

The density may be known based on information provided to the system 200 through a user input or via a wireless message. This volume is then monitored over a period of time to determine the average flow rate that is being directed to an infusion pump 206. The infusion pump 206 is controlled by an infusion device 208, which may control additional infusion pumps in addition to the infusion pump 206. The infusion container 202 is connected via a tubing 204 to the infusion pump 206. The hanger 300 includes circuitry and a microprocessor (illustrated in FIG. 3) that calculates the fluid volume by converting the measured weight signal. The calculated fluid volume is communicated using either a wired or wireless signal 212 from the hanger 300 to the infusion device 208 to verify the expected flow rate. The hanger 300 notifies the infusion device 208 of a need to evaluate an abnormal condition. Prior to the start of the infusion process, the infusion device 208 sends a signal data 210 to the hanger 300 regarding the programmed infusion rate. Although shown as separate devices in FIG. 2, in some implementations, the infusion pump 206 and the infusion device 208 may be a single device.

FIG. 3A shows an example device for determining a fault condition in an infusion process, according to aspects of the subject technology. Load cell (or gravimetric) technology is used to measure the weight of the fluid during an infusion process. The volume of the infused fluid is then calculated using a known fluid density of the fluid. The density may be known based on information provided to the system 200 through a user input or via a wireless message. The exemplary hanger 300 includes a support hook 302, for securing the hanger to a supporting structure, such as an IV pole or a pole clamp (associated with, e.g., an infusion pump, or accessories or auxiliary devices associated with the infusion pump). Other types of support mechanisms may also be used. The hanger 300 includes a housing 316, within which an internal frame 322 is placed. According to various implementations, the internal frame 322 houses a battery 318, and may be rectangular shaped such that its length spans a significant length of the housing 316. Internal frame 322 may include an opening for replacement of the battery and a latch for opening a locking mechanism which secures the battery in place. In the depicted example, the internal frame is configured such that the opening reveals the battery to a user, so that the batter is immediately identifiable as present when the housing 316 is opened by the user. The internal frame 322 may be positioned within housing 316, coupled to a guide element 320 and a strain gauge conditioning housing 310. The guide element 320 may further include an internal housing that houses a wireless communication device (e.g., a Bluetooth wireless communication circuit), which connects with other wireless communication-enabled devices external to housing 316, and facilitates communication between those external devices and a microprocessor located within the strain gage conditioning housing. The hanger 300 also includes a load cell 312 coupled to an IV bag hook 314. The hanger 300 also includes a switch 306 and a swivel 304 that is connected to an elastomer isolator 308.

The elastomer isolator 308 is placed between the upper supporting hook 302 and the hanger frame 322 to minimize vibration influences by isolating the weighing system from the supporting structure (e.g., the IV pole). Vibrations can be caused by either shock inputs or steady state vibration. Shock inputs can be caused by sudden movements of the pole, or impacts during movement. Steady state vibration can be caused by mechanical equipment operating near the hanger 300. In general, data processing software executed by the microprocessor can incorporate low pass filtering to remove some of the vibrations, together with averaging, and comparison of pre-shock and post-shock signals to remove shock inputs. Filtering can be applied to discount or disregard frequencies above the pumping frequency as part of flow rate or volume monitoring.

The swivel 304 may function to direct the weight load from IV container along the principal axis of the load cell 312. By directing the weight load from IV container along the principal axis of the load cell 312, and minimizing (e.g., eliminating) lateral forces, other non-axial loads or torsion moments, more reliable weight measurements of the IV infusion container may be made. The hanger 300 incorporates the swivel 304 and an upper attachment shaped to ensure that the load applied to the hanger 300 is applied axially, with no side or twist loads applied. Accurate measurements of infusion fluid output is improved when the hanger 300 is capable of maintaining a vertical orientation of the principal axis of the load cell 312; and insuring the fluid container is suspended freely from the load cell 312 without any additional support.

The weight measurement resolution may be as high as 0.2 grams, to allow the volume of fluid displaced within one pump cam revolution to be measured. IV containers may have volumes as high as 1000 mL. In some implementations, the load sensor may have the capability to measure the full capacity 1000 mL fluid container, which can contain an equivalent weight of 998 grams of water.

The housing 316 encloses the load cell 312, electronics, and power supply systems. In some implementations, the hanger 300 has a sealed construction with openings for the upper and lower hook elements (e.g., the support hook 302 and the IV bag hook 314, respectively). The sealed construction prevents fluid ingress and the rounded edges in the housing 316 allow cleaning. The housing 316 may be made of a material (e.g., a plastic resin such as VALOX™ FR Resin 364 from SABIC or the like) that is tolerant to medical-grade cleaning solutions and has impact resistance against inadvertent drops.

In some implementations, the battery 318 provides a nominal 5 volts, with sufficient capacity to allow operation for 96 hours between charges. A standard USB connector may be provided to charge the battery 318 via a USB charging port. In some implementations, the hanger 300 includes a charging system that incorporates an inductive charging coil similar to charging coils used for phones or other consumer electronic devices. Using inductive chargers, the hanger 300 may eliminate the need for connectors thus minimizing the numbers of openings in the housing 316 that are susceptible to fluid ingress and reducing the amount of maintenance and cleaning needed for the hangar 300.

The electronics in the hanger 300 incorporate the load cell strain gage conditioning circuit 310 and an A/D converter; a microprocessor; a data store such as a non-volatile static random access memory (nvSRAM) to save calibration values, rate, and weight data (e.g., 20 minutes of weight date); proprietary or standards compliant (e.g., BLUETOOTH low energy (BLE)) wireless communication system 320; a battery charging system; a light emitting diode (LED) indicator for battery charge, and operational status, or optional display. The display may show the desired medication and flow rate, as an additional way of confirming various parameters in the infusion process.

The hanger 300 may have Bluetooth or other personal area network (PAN) communication capabilities. In some implementations, BLE (Bluetooth Low Energy) or similar PAN technology (e.g., Zigbee) is used because of its low power consumption. The PAN capabilities allows communication between the hanger 300 and control unit 14 of an infusion device 208 (e.g., a PCU). In some implementations, the infusion device is able to receive weight information from multiple different hangars. For example, six hangers (e.g., from four infusion pumps and two secondary infusion bags) for the same patient may establish communications with the infusion device.

The IV container is placed on a pole (or other structure) within close proximity of the infusion device (e.g., three feet). This proximity is within a communication range of the PAN communication system. Data transfer from the hanger 300 to the PCU may accommodate a maximum of six samples per second. In some implementations, the PCU may transfer information received from the hangar 300 or for transmission to the hangar 300 using a hospital's wide area network or local area network (e.g., Wi-Fi or cellular) for interoperability with other systems, if desired.

The switch 306 of hanger 300 is operational for turning the electronics, such as the microprocessor and the Bluetooth communication electronics within hanger 300 off when not in use to conserve battery power. The hanger 300 may also include one or more indicators (e.g., one or more light-emitting diodes (LEDs)) disposed on an outer portion of the housing 316 to indicate that the hanger 300 is on, the battery charge level, status and any error conditions that may need attention.

In some implementations, the load cell is able to handle an overload force, to account for cases where the IV administration set (or portion thereof) is pulled unintentionally. For example, the load cell is able to sustain a force equivalent to the load required to pull the IV spike from the IV bag or to separate the set from fitments, which can be approximately 35 N (8 lbf). In this way, the load sensor would be able to sustain a nominal 4 kg load without damage.

In some implementations, the weight sensor is incorporated as part of the IV bag. Since the bags are generally disposable and not reused for multiple infusions, the weight sensor and circuitry would be low cost and imbedded into the bag and would not be removed from the bag once it is used.

FIG. 3B depicts an external view of an example device shown in FIG. 3A. The hanger 300 includes the support hook 302, the housing 316, and the IV bag hook 314.

An out-of-range or fault condition can include an over-infusion or an under-infusion of medication. A number of factors can cause inaccuracies during infusion including, for example, (1) varying tolerances associated with many individual components in each pump can lead to (e.g., significant) pump-to-pump variations; (2) variations in the environment, e.g., temperature, relative humidity; (3) variations in fluidic properties of the medication used in the infusion, e.g., viscosity, density; (4) height of the IV bag; (5) variations in the disposable administration sets.

Pump-To-Pump Variation

An infusion pump is composed of dozens, if not hundreds, of components assembled together. Dimensional variations during manufacturing of the individual components, although small on an individual component basis, stack up in an assembly and result in a difference in performance from one pump to another. For example, a cam follower on one pump may be longer than on other pumps. Longer cam follower provides better contact with the disposable set during infusion and therefore delivers more fluid compared to what a pump with shorter cam follower can.

Environmental Setting

Infusion pumps are used in a variety of climate settings depending on the country and the setting (e.g. hospital, home, air-conditioned area, etc.) in which they are used. These environmental factors may affect the individual components of the pumps (e.g., dimensional expansion or contraction) or affect the disposable sets which may contribute to infusion inaccuracies.

Medication Fluid Properties

An infusion pump can work with a large variety of fluids. Water, glucose, and blood—not to mention the many medication formula—are among the different types of fluid that can be delivered using an infusion pump. The differences in viscosity and density, among other physical characteristics of the infusion fluid, can affect an accuracy of the infusion volume measured by the infusion pump.

IV Bag Height

Accuracy of the infusion volume can be affected by the height of IV bag relative to the pumping mechanism of the infusion pump. Higher height differences result in a higher hydraulic head and lower height differences result in a lower hydraulic head. Assuming all other factors remain constant, a lower hydraulic head results in a smaller actual volume infused compared to a higher hydraulic head.

In some accuracy test setups, manufacturers specify a height of the IV bag relative to the pumping mechanism used in conducting the tests prescribed by Clause 201.12.1.102 of IEC 60601-2-24:2012. In other words, a manufacturer may specify the parameters and configurations of the test set-up to determine the accuracy of the pump in delivering medication. In an actual patient-care setting, IV pole space may be limited, especially for an IV pole carrying multiple infusion pumps and/or multiple IV bags. The height difference between the fluid bag and the pumping mechanism may thus not match those used in the standard accuracy test setup, which in turn affects the accuracy of measurements of infusion volumes infused by the infusion pump. For example, when the height of the IV bag is higher, relative to the pumping mechanism, in an actual patient care setting, as compared to the standard accuracy test setup, the infusion flow rate may be higher (due to the higher hydraulic head) than the benchmark flow rate used during the standard accuracy test setup. Conversely, when the height of the IV bag is lower, relative to the pumping mechanism, in an actual patient care setting, as compared to the standard accuracy test setup, the infusion flow rate may be lower (due to the lower hydraulic head).

Variations in Disposable Sets

Disposable sets vary in length, internal diameter, presence of filters or junctions. A fluid flowing through a disposable set having (i) a smaller internal diameter, (ii) a longer length, or (iii) a presence of filters or (iv) a presence of junctions may experience an increase in fluidic resistance while traversing the disposable set. These additional resistance in the tubing line may cause variations in medication delivery accuracy (e.g., the infusion flow rate may be reduced due to an increase in fluidic resistance). Conversely, a fluid flowing through a disposable set having (i) a larger internal diameter, (ii) a shorter length, or (iii) lacks a filter or (iv) lacks a junction may experience a decrease in fluidic resistance while traversing the disposable set. The reduction of resistance in the tubing line may cause infusion flow rate to be increased.

Figure 3C:
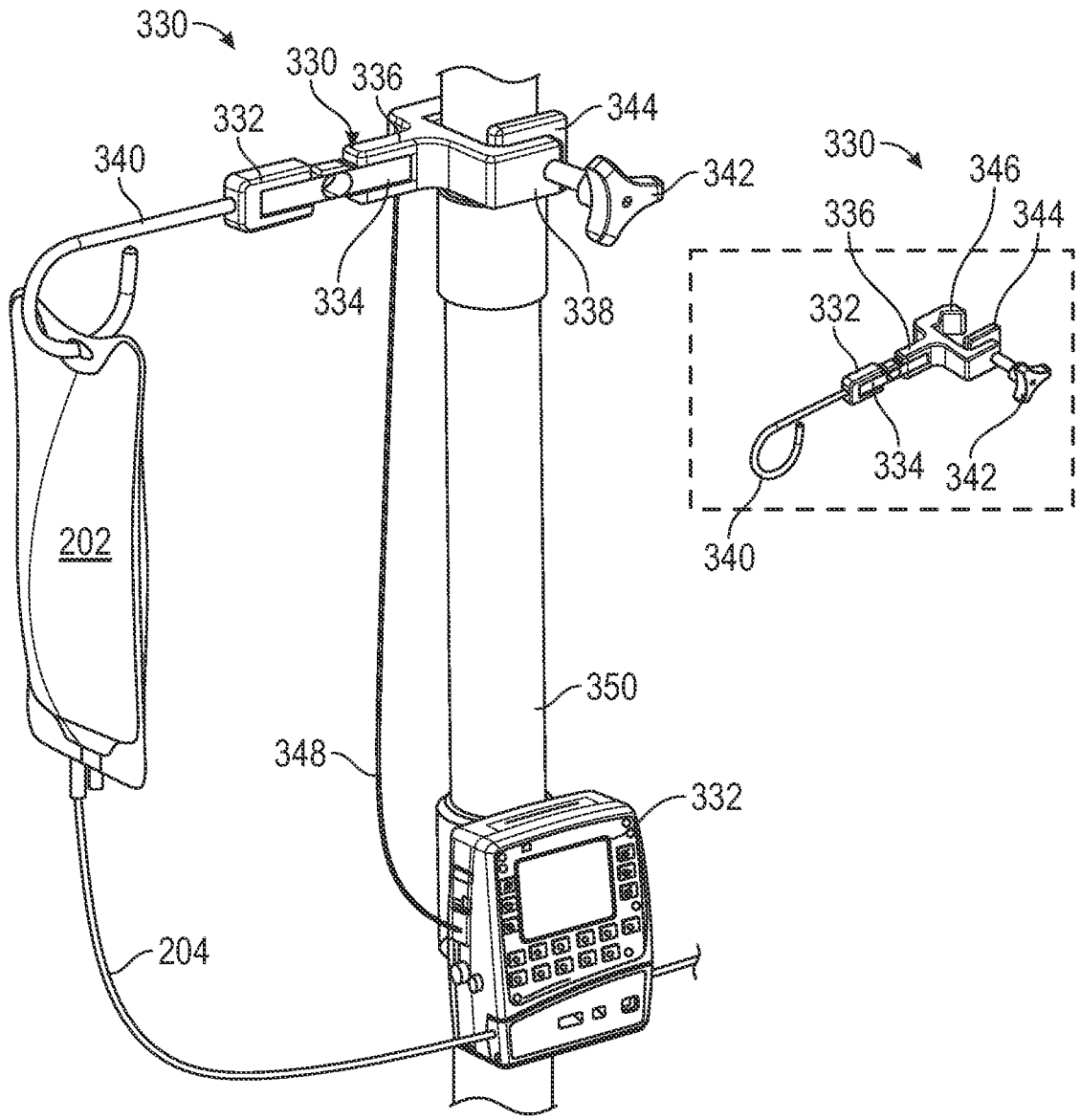
FIG. 3C depicts an example device for determining a fault condition in an infusion process, according to aspects of the subject technology.

FIG. 3C shows an example device for determining a fault condition in an infusion process, according to aspects of the subject technology. A hanger 330 includes a fastening mechanism 342, for securing the hanger 330 to a supporting structure, such as an IV pole 350. In some implementations, the fastening mechanism 342 is a pole clamp (associated with, e.g., an infusion pump, or accessories or auxiliary devices associated with the infusion pump). Other types of support mechanisms may also be used. The hanger 340 includes a first component 332 that is connected to an IV bag hook 340, and a second component 336 that is connected to portion 338 that engages the fastening mechanism 342. The first component 332 is not directly connected to a second component 336. Instead, the first component 332 is connected to the second component 336 only through a load cell, for example, a shear load cell 334. Shear load cells are suitable for measuring compressive forces. In some implementations, the shear cell includes a spring body having a piece of metal, which deforms under the influence of the force (e.g., compressive force) and returns to its original state when the force is withdrawn. The deformation is registered via a strain gauge connected to the metal piece and converted into an electrical signal. Based on calibrations, measurements of the shear load are converted into weight (or mass) measurements (e.g., grams, pounds). Having the first component 332 be connected to the second component only via the shear load cell 334 ensures that most (e.g., all) of the IV bag 202's weight is measured by the shear load cell 334.

In some implementations, the shear load cell 334 provides the measured weight data to an infusion pump 332 via an electric signal over a wired connection 348. In some implementations, the shear load cell 334 provides the measured weight data to an infusion pump 332 wirelessly (e.g., the wired connection 348 is not used). In such implementations, the shear load cell 334 includes a wireless communication device (e.g., a Bluetooth wireless communication circuit), which connects with other wireless communication-enabled devices external to the hanger 330, and facilitates communication between those external devices and the shear load cell 334. Based on the measurements from the shear load cell 334, the infusion pump 332 is able to correct and/or adjust a force, in real time, or near real-time, that is applied on the tubing 204 of an IV administration set, to help ensure that infusion is occurring at a desired rate (e.g., no over-infusion and no under-infusion).

According to various implementations, the hanger 330 communicates with the infusion pump 332 and, by measuring the weight reduction in the IV bag 202 (e.g., via the formula volume=mass/density), allows an actual amount of volume infused to be determined. By continually providing weight feedback to the infusion pump 332, the shear load cell 334 in the hanger 330 allows the infusion pump 332 to adjust, if needed, one or more operational parameters (e.g., motor speed) to deliver a correct expected infused volume at any given time. When the operation parameter is the motor speed, the motor speed may be decreased if there is over-infusion. The motor speed may be increased if an under-infusion is detected. The adjustment of the motor speeds helps reduce pump delivery inaccuracies. In some implementations, motor speeds are pre-determined at respective infusion flow rates. The infusion pump can include software that allows adjustment of the motor speed to be faster or slower than the pre-determined speed if there is a mismatch between (i) an actual volume infused at a given time and (ii) an expected volume infused at the given time.

In some implementations, the hanger 330 checks for severe infusion inaccuracies, and provides early detection, alarm, and/or stops infusion, if necessary, depending on a workflow of the infusion pump as defined by the manufacturer of the infusion pump. In some implementations, severe conditions of infusion inaccuracies include, for example, 40% under-infusion (or at other parameters defined by a manufacturer). The ability to detect infusion volume inaccuracies in real-time minimizes (e.g., avoids) potential harm to the patient as early as possible.

The inset in FIG. 3C shows the hanger 330 before it is attached to the IV pole 350. The portion 338 includes a notch 346 to allow for better engagement with the IV pole 350. The fastening mechanism 342 also includes a flat component 344 that allows the compressive force applied via the fastening mechanism 342 to be more evenly spread over a larger portion of the IV pole 350, for ensuring a more secured attachment of the hanger 330 to the IV pole 350. By adding to the hanger 330 to the system (including the infusion pump) via plug-and-play, the hanger 330 adds capability of measuring infused volume on a compatible pump.

Figure 3D:
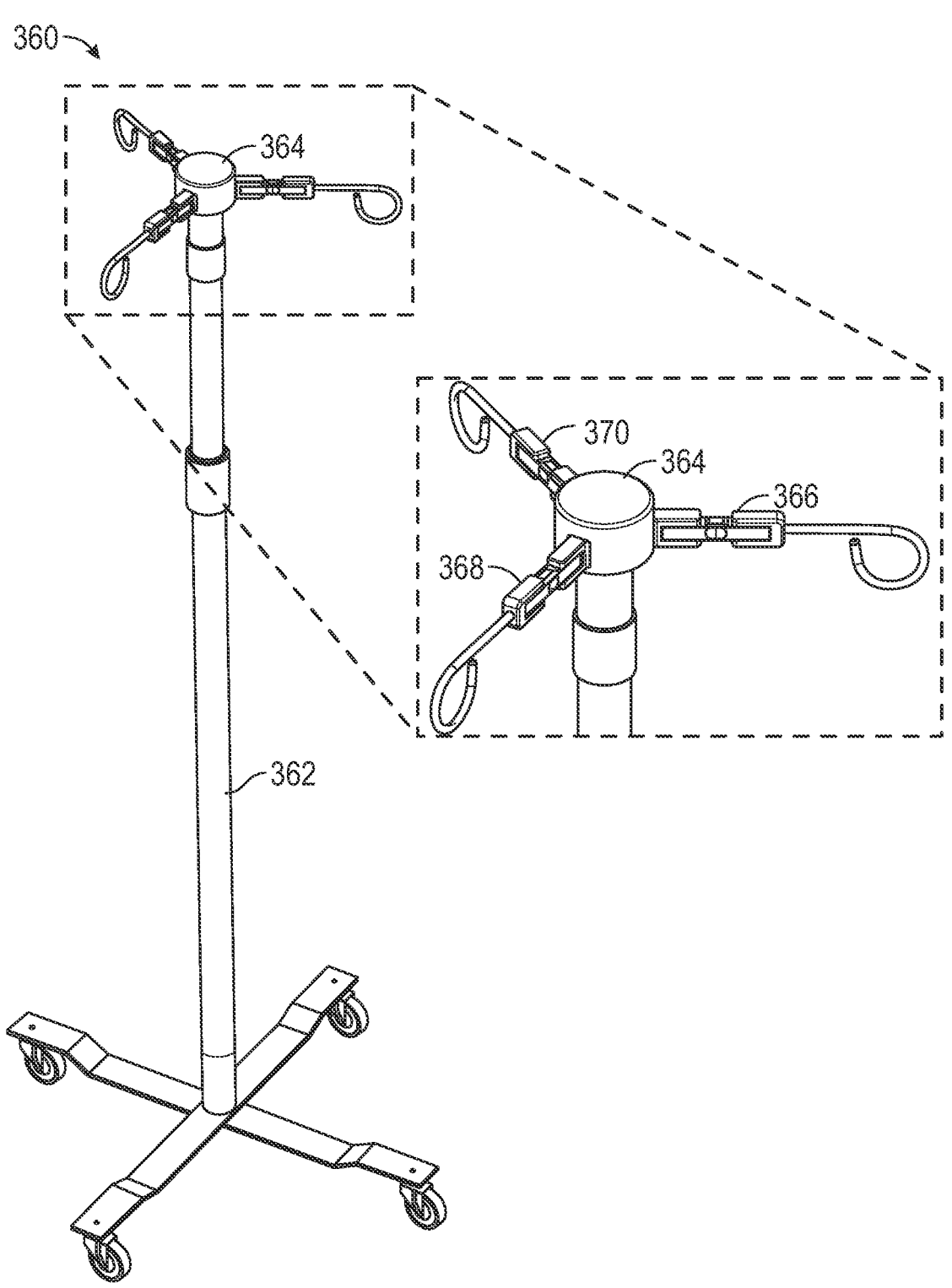
FIG. 3D depicts an example device for determining a fault condition in an infusion process, according to aspects of the subject technology.

FIG. 3D shows example devices for determining a fault condition in multiple infusion processes, according to aspects of the subject technology.

A hanger assembly 360 includes a number of hangers (e.g., three) that are configured to determine a fault condition in multiple infusion processes. Unlike the hanger 330 that includes its own fastening mechanism 342, hangers 366, 368, and 370 are directly attached to a support cap 364 disposed atop an IV pole 362. The hangers 366, 368, and 370 each includes a shear load cell, supported by two disjointed housing components, similar to the first component 332 and the second component 336 of the hanger 330.

In some implementations, a height of the smart IV pole 362 is varied to adjust an infusion rate of an infusion process. In some examples, the smart IV pole 362 includes an actuator that allows a shaft length of the smart IV pole to be lengthened or shortened. Extending the IV pole 362 increases a height of an IV bag supported by the hanger assembly 3620 and increases a rate of infusion, assuming all other conditions are kept constant. In some implementations, the support cap 364 is a split cap that allows heights of the hangers 366, 368, and 370 to be adjusted independently. In some implementations, the IV pole 362 is a smart IV pole that is packaged as a sub-system having plug-and-play communication capabilities with compatible infusion pumps. Communication between the load cell 366 and an infusion pump can be wired or wireless as described in FIG. 3C. When communication is over a wired connection 348, the wired connection may be embedded within the body of the IV pole 362 (e.g., traversing the cylindrical shaft).

In some implementations, the smart IV pole 362 can communicate height information to the infusion pump, which then can be used in the analysis to determine how any over-infusion or under-infusion may be corrected.

For example, when the weight measurements obtained from the shear load cell 334 indicates there is a correctable under-infusion (e.g., a difference between the actual volume infused and the expected infused volume is not significant enough to cause a termination of the infusion process), the infusion pump can determine if the smart IV pole 362 is already at its maximum height. Instead of simply increasing the motor speed to increase the infusion rate, the hydraulic head of the IV bag may be increased to increase the infusion rate. If the smart IV pole 362 is not at its maximum height, the infusion pump can send a control signal to an actuator in the smart IV pole 362 to cause the pole to increase in height. The height of the smart pole can be adjusted alone, or in combination with a change in the motor speed of the infusion pump. For example, instead of increasing the motor speed by 10%, the height of the smart IV pole may increase by an inch. Alternatively, the motor speed may increase by 5% and the height of the smart IV pole may increase by half an inch.

For example, when the weight measurements obtained from the shear load cell 334 indicates there is a correctable over-infusion (e.g., a difference between the actual volume infused and the expected infused volume is not significant enough to cause a termination of the infusion process), the infusion pump can determine if the smart IV pole 362 is already at its minimum height. Instead of simply decreasing the motor speed to decrease the infusion rate, the hydraulic head of the IV bag may be decreased to decrease the infusion rate. If the smart IV pole 362 is not at its minimum height, the infusion pump can send a control signal to the actuator in the smart IV pole 362 to cause the pole to decrease in height. The height of the smart pole can be adjusted alone, or in combination with a change in the motor speed of the infusion pump. For example, instead of decreasing the motor speed by 10%, the height of the smart IV pole may decrease by an inch. Alternatively, the motor speed may decrease by 5% and the height of the smart IV pole may decrease by half an inch.

In some implementations, the smart IV pole 362 includes a local processor that processes the weight measurements obtained from the shear load cell 334, and the local processor sends control signals to the actuator to adjust the height of the smart IV pole, independently of the infusion pump.

In some implementations, a clinical workflow process may incorporate the following steps:

First, the hanger 300 is turned on (using the switch 306) and placed on an IV pole using the IV pole hook 302. The microprocessor of hanger 300 initializes a weight to zero by a "set zero" function that is employed in the software to initialize the system prior to hanging the IV bag. An indicator (not shown) lights up when the hanger 300 is ready to receive an IV bag at the IV bag hook 314. When an empty fluid container is swapped for a full one, the PCU may display a message to the clinician to reset with the system with the hanger zeroed, prior to continuing the infusion.

A caregiver (e.g., a nurse) scans the IV container, the hanger 300, an identification for a patient, and the infusion pump to associate all constituents in the infusion process. The hanger 300 communicates with the PCU to indicate a volume measured for the IV container and to display medication information on a display of the PCU. In implementations, the hanger 300 includes a display connected to the microprocessor. The display may display medication information associated with a medication container hanging from hook 314. According to various implementations, the microprocessor of the hanger 300 may be associated with a scanning device configured to scan medications containers (e.g., IV bags). Scanning an IV bag or other medication container may transmit the medication information, including an identifier for the medication, to the microprocessor, which may then index the identifier with operational parameters and formulas used to perform the calculations disclosed herein. According to some implementations, the microprocessor of hanger 300 may be in communication with a PCU, and medication information may be transmitted between the microprocessor and the PCU over a wireless connection. For example, the microprocessor may be paired to the CPU via the PAN circuitry. Associating the hanger 300 and an IV container and a PCU provides associativity of the IV container to a pump channel of the infusion device operated by the PCU. According to some implementations, the PCU may send flow rate information to the hanger 300 and signals the hanger 300 to begin the measurement process.

During the infusion process, confirmation of the volume of medication infused, the remaining amount of the medication, and flow rate information can be transmitted to the PCU from the hanger 300. The wireless communication circuitry in the hanger 300 may also deliver the information to the nurse's station. The system operates autonomously unless an out-of-range condition (e.g., a fault condition) occurs which causes the PCU to send out an alarm for a nurse to evaluate the fault condition. In some implementations, the PCU includes closed loop infusion control capabilities and modifies one or more operation parameters of the infusion pump based on the signal received from the hanger 300.

In some implementations, the microprocessor of the hanger 300 may generate flow rate information based on detected weights or volumes over time. This flow rate information may be provided to the PCU or compared, by the hanger 300, with desired flow rate information received from the PCU. If the generated rate does not correspond to a desired flow rate, the device performing the correspondence check (e.g., PCU, pump, or hanger) may adjust one or more physical element associated therewith. The adjustment may include activating a perceivable indicator, adjusting a display or other user interface, adjusting power supply or mode, stopping or slowing a motor, or the like.

If the infusion device receives an input to change the flow rate during an ongoing infusion process, the PCU may communicates with the hanger 300 to change the detection conditions. When the flow rate is changed, the changed rate may effect the expected weight change over time. There may be some initial differences in the initial fill cycle and the system may need some time to adjust to determine and verify the new flow rate. Typically, flow rate changes are minor. However in cases where the flow rate is drastically changed (e.g., from 1 ml/hr to 999 ml/hr), the magnitude of the effect can be more significant, and the detection processing may include a delay to allow stabilization of the signal. The delay may be a static configuration value for the system or dynamically generated based on one or more values available to the system such as medication type, magnitude of the rate change, or care area where the infusion is occurring.

Figures 4A, 4B, 4C, 4D:
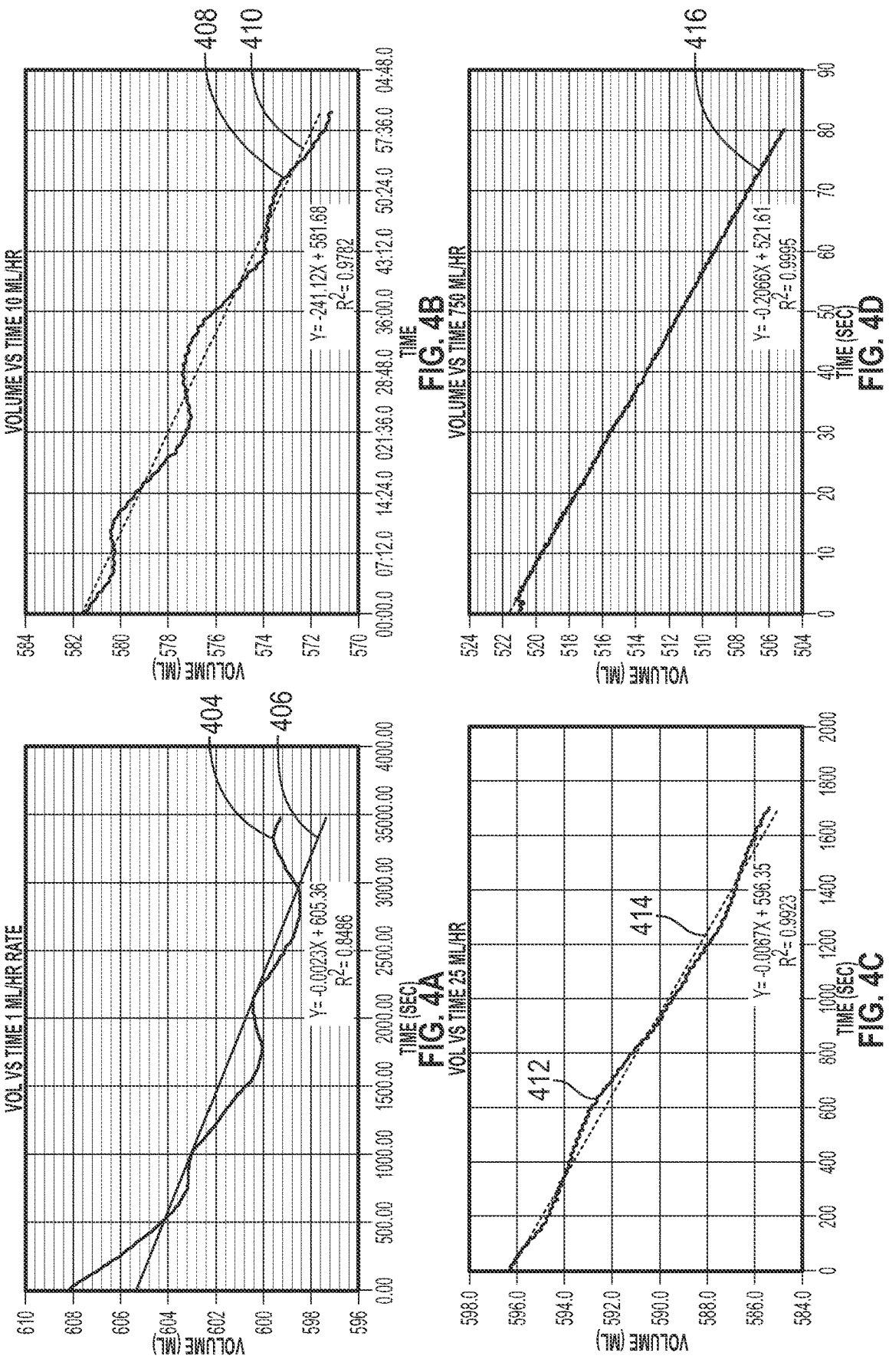
FIGS. 4A-4D depict volume data as a function of time for various flow rates, according to aspects of the subject technology.

FIGS. 4A-4D depict volume data as a function of time for various flow rates, according to aspects of the subject technology. During operation at a typical low flow rate, the weight sensor may see a signal similar to that shown in the FIG. 4A. The signal has a definitive characteristic that shows periods of no delivery of fluid, followed by the fill portion of the cycle which shows a rapid delivery to fill the pumping chamber. If the signal is evaluated and compared to what is expected during the fill portion of the cycle, a determination can be made if the pump is operating correctly during the period of just one pumping cycle, and thus reducing the time to detect an anomaly. In FIG. 4A, a curve 402 shows the measured flow volume at a flow rate of 1 ml/hour. A line 404 represents the linear regression for the flow volume measured in the curve 402.

In FIG. 4B, a curve 408 shows the measured flow volume at a flow rate of 10 ml/hour. A line 410 represents the linear regression for the flow volume measured in the curve 408. In FIG. 4C, a curve 412 shows the measured flow volume at a flow rate of 25 ml/hour. A line 414 represents the linear regression for the flow volume measured in the curve 412. In FIG. 4D, a line 416 shows the measured flow volume at a flow rate of 750 ml/hour. The regression line for the line 416 largely coincides with the measured line 416. The measurement results shown in FIG. 4A through FIG. 4D indicate that an average flow volume deviation can be harder to detect at lower flow rates (e.g., 1 ml/hour) as compared detecting deviations at higher flow rates (e.g., 750 ml/hour).

Figure 5A:
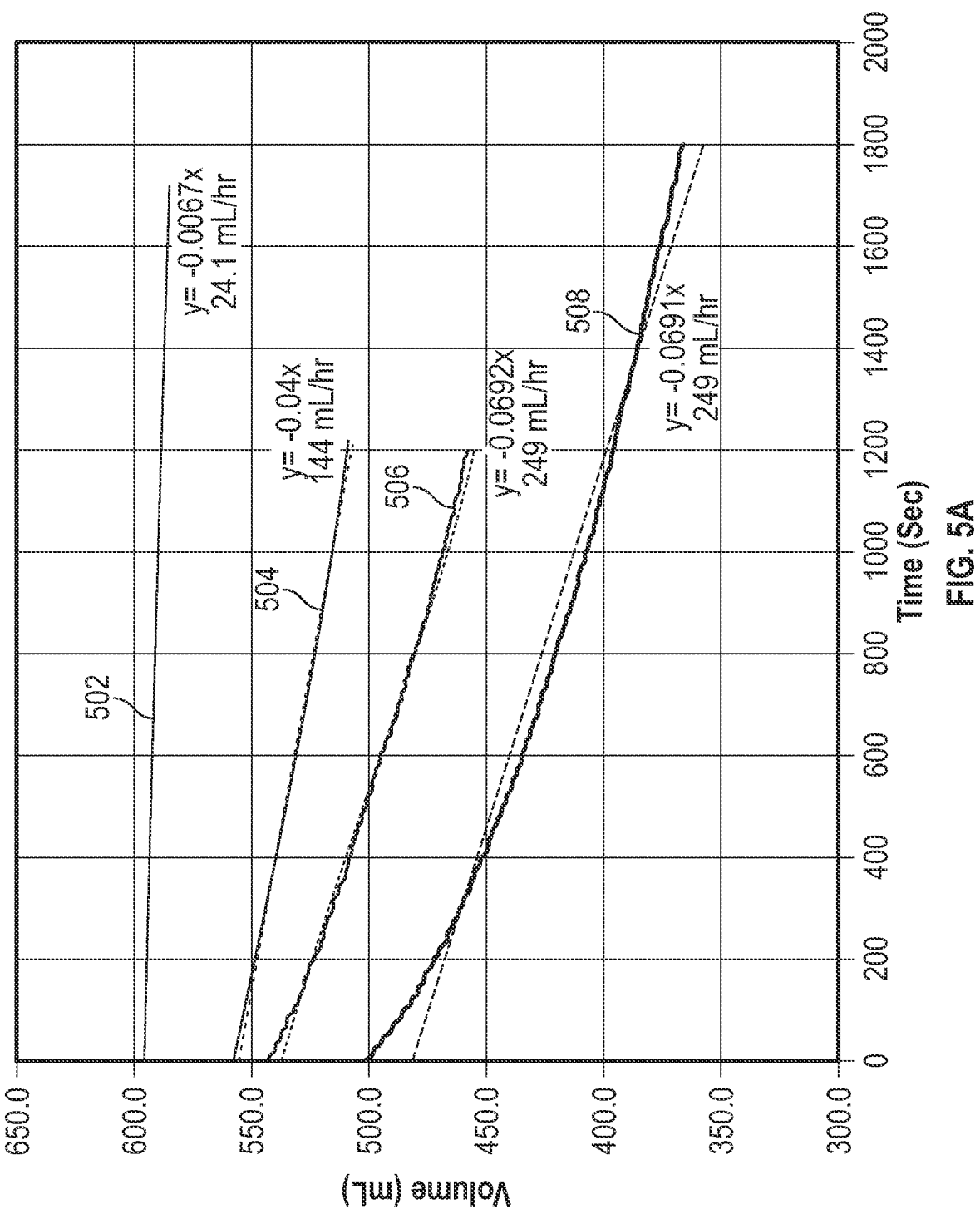
FIGS. 5A-5C depict volume data as a function of time for various flow rates when a fault condition exists, according to aspects of the subject technology.
Figure 5B:
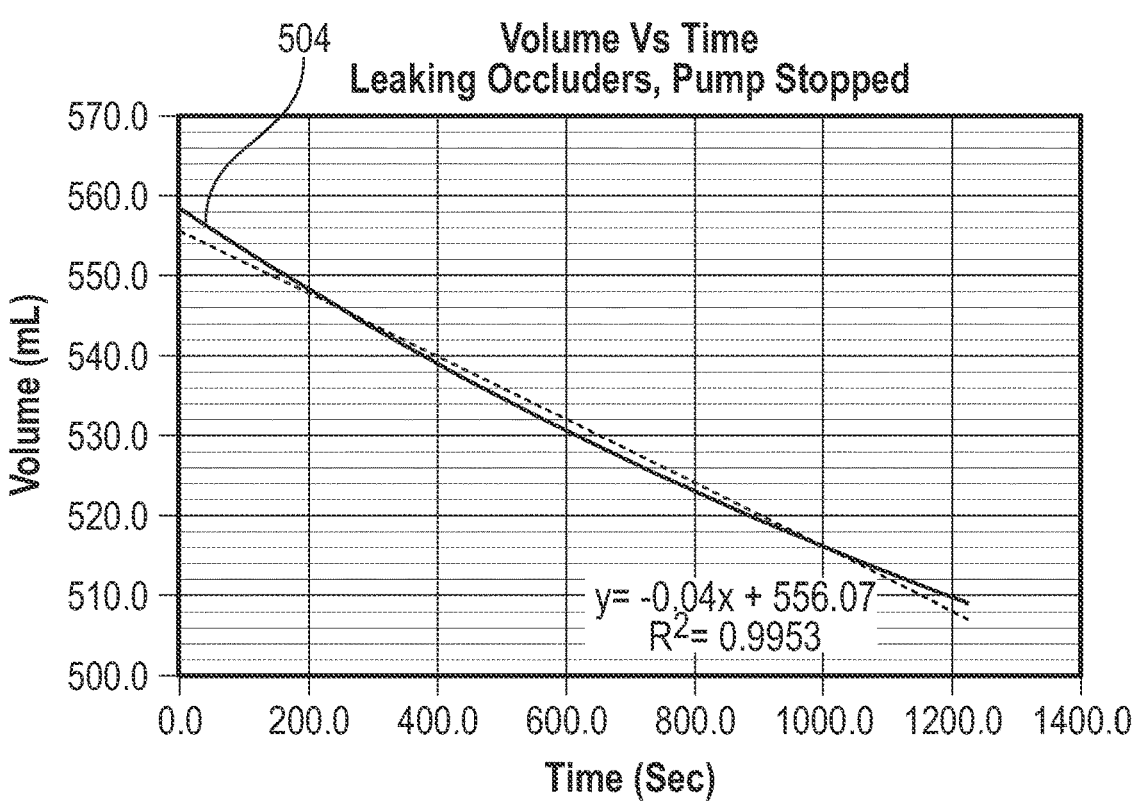
Figure 5C:
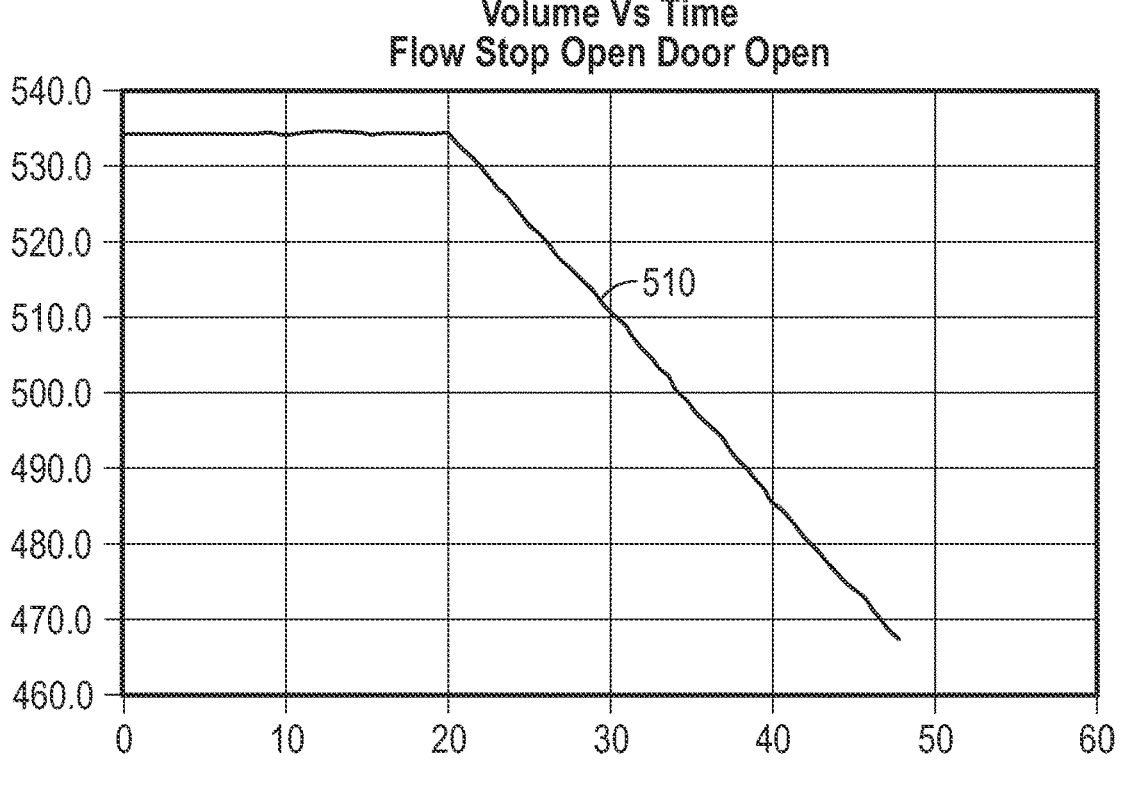

FIGS. 5A-5C depict volume data as a function of time for various flow rates when a fault condition exists, according to aspects of the subject technology. FIG. 5A shows a comparison of experimental volume measurements under different pump conditions. A curve 502 shows the measured volume as a function of time for a pump infusing at 25 ml/hour under normal operation conditions. A curve 504 shows the measured volume as a function of time for a pump infusing at 25 ml/hour when the infusion pump has a leaking occluder or leaking occluder finger 211 (FIG. 2) and the pump has been stopped. Leaking occluders may be caused by damaged components of the pump, or when the IV tubing is not completely pinched off to produce a seal.

A curve 506 shows the measured volume as a function of time for a pump infusing at 25 ml/hour when the infusion pump has a leaking upper occluder and the pump continued pumping. A curve 508 shows the measured volume as a function of time for a pump infusing at 25 ml/hour when the infusion pump has two leaking occluders (e.g., upper occluder and lower occlude) and the pump continued pumping. The curve 508 shows a larger drop in volume compared to the curve 506 because both occluders were leaking. The curve 508 also shows a larger drop in volume compared to the curve 504 because the pump did not stop (as was the case in curve 405). The curves 504, 506, and 508 in FIG. 5A show significant differences compared to the curve 502 recorded from a normal operating pump at 25 ml/hr.

FIG. 5B shows the curve 504 in enlarged view. The leaking occluders are causing an effective flow of 144 mL/hr even though the pump is off. FIG. 5C shows a curve 510 depicting the change in volume of fluid in the infusion container as a function of time when both the flow stop of the administration set and the door of the pump are open. FIG. 5C shows that the hanger 300 is still able to detect changes in the volume of the infusion container when, for example, the pump is turned off but both the flow stop of the administration set and the door of the pump are open. When the pump is turned off, it is unable to issue the "flow stop open" alarm. Nonetheless, the hanger 300 is still able to detect a fault condition and issue an alarm to a caregiver. The fault scenarios illustrated in FIG. 5B and FIG. 5C show that the flow rates were sufficient to be detected by the hanger 300. The hanger 300 thus adds another measure of safety for situations in which fault conditions are not detected in the case where the pump is turned off or otherwise experiences a failure.

Figure 6A:
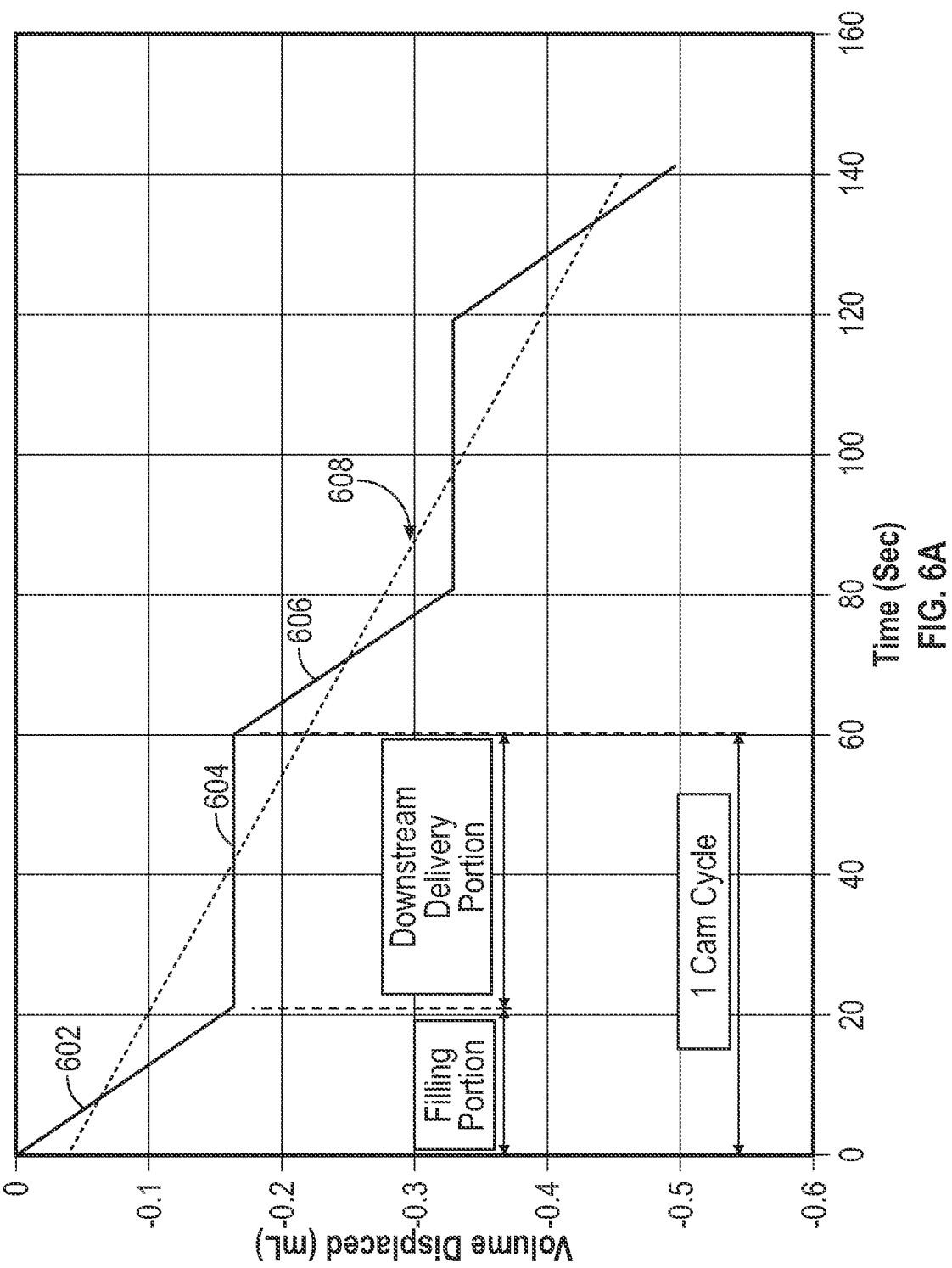
FIG. 6A is a conceptual diagram illustrating an average flow rate for a cam cycle, according to aspects of the subject technology.

In some implementations, the infusion pump operates in a cyclical fashion, with a fill phase, and a delivery phase in a single pump cycle. During the fill phase, fluid is received from the IV container into the pumping segment of the IV tubing set. The pumping segment is the part of the administration set that is squeezed by the pump fingers. At this time, the upstream occluder is opened and the lower occluder closed so no flow is delivered downstream. The pump cycle then transitions into the delivery phase, in which the upper occluder closes and the lower occluder opens. During this time, the pump displaces the fluid in a controlled manner to deliver uniform flow to the patient, but no fluid is received from the IV container, as shown in FIG. 6A. The flow delivered on the downstream side is important to drug delivery. The hanger 300, in contrast, verifies the fill phase of the pump cycle.

To reasonably assess the delivery flow rate, a certain number of cycles is used so that the average fill rate approximates the average delivery flow rate. In some implementations, between four to eight cam cycles are used so that the fill flow rate sufficiently approximates the delivery flow rate. This allows a reasonable correlation of the downstream flow rate when measuring the upstream flow rate. Since the flow rate is dependent on the cam RPM, the average flow rate assessment is time dependent. At low flow rates, using multiple cam cycles may take a significant amount of time to detect flow rate inaccuracies of 20%. Testing with non-conforming pumps with known various faults such as damaged pump components, show very large flow rate errors, and in these cases the weight based system is able to detect fault conditions in the non-conforming pumps in very short periods of time, allowing for notification and intervention from the user.

FIG. 6A is a conceptual diagram illustrating an average flow rate for a cam cycle, according to aspects of the subject technology. The average flow rate represents the average between the fill volume and delivery volumes over time. During the fill phase, a slope 602 showing a drop in the fluid volume in the IV container is measured. During the delivery phase, a constant volume 604 is measured. During the next fill phase, a slope 606 caused by a drop in the volume of the fluid in the IV container is observed. A slope 608 of the curve is found by linear regression of the best fit of measurement points and represents the average flow rate. The slope 608 is negative because the fluid volume (measured weight) is decreasing as the infusion fluid is being consumed by the pump (by delivering the infusion fluid to the patient). In some implementations, uniformity in a downstream flow rate is enhanced by controlled movements of a primary finger in the infusion pump and is helped by a compensating finger 209 (FIG. 2) in the infusion pump which continues to deliver some flow during the fill portion of the cycle.

Figure 6B:
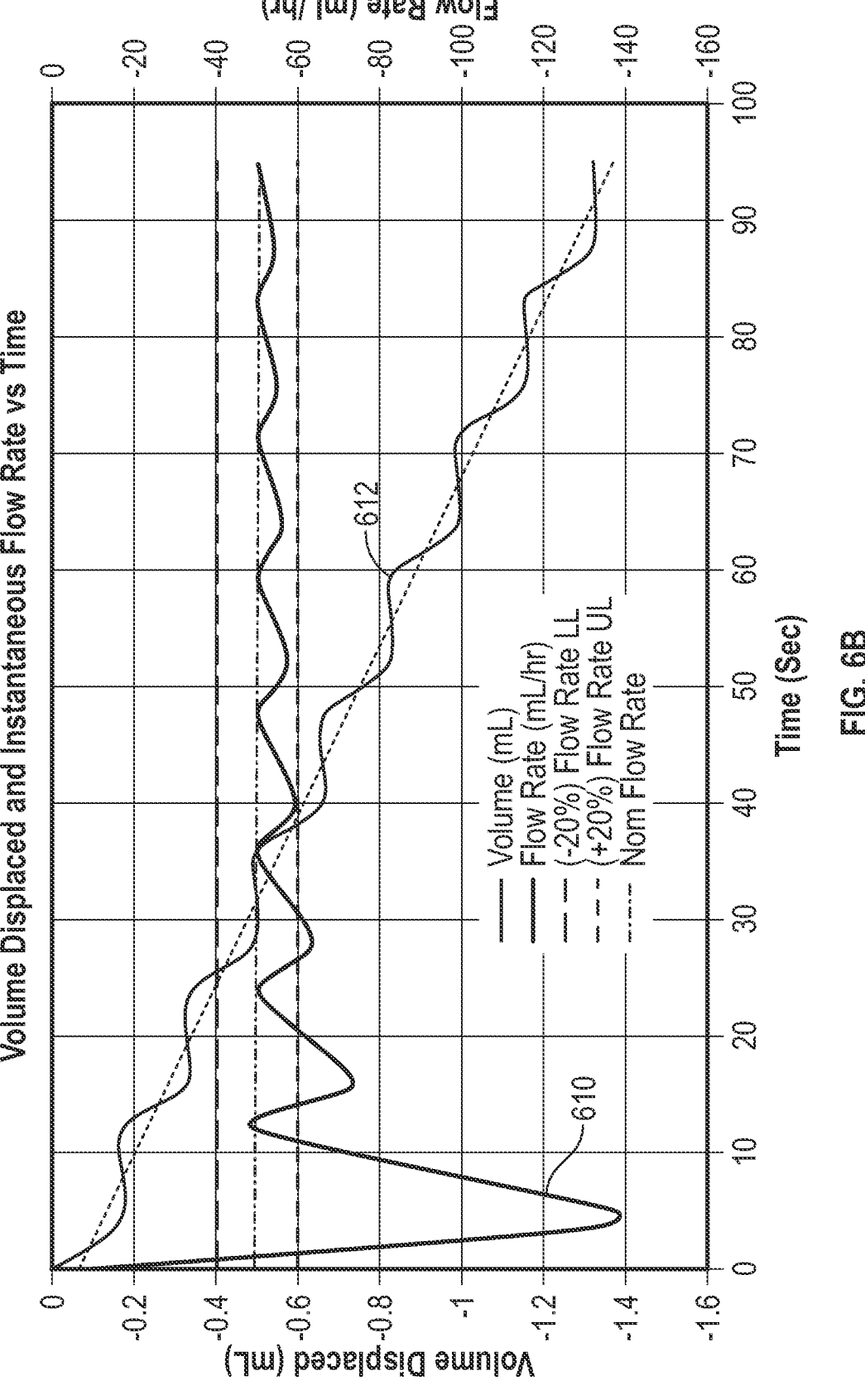
FIG. 6B depicts volume and flow rate data as a function of time, according to aspects of the subject technology.

FIG. 6B shows volume and flow rate data as a function of time, according to aspects of the subject technology. A curve 610 shows the cumulative flow rate, while a curve 612 shows the volume displaced from the IV container. FIG. 6B also shows that as the number of cam cycles increases, the cumulative flow rate stabilizes with less variability. For example, by about the sixth cam cycles, the flow rate approaches the mean accumulated flow rate.

FIG. 7 depicts an example method for determining a fault condition during an infusion process, according to aspects of the subject technology. For explanatory purposes, the various blocks of example method 700 are described herein with reference to FIGS. 1-6B, and the components and/or processes described herein. The one or more of the blocks of method 700 may be implemented, for example, by one or more computing devices such as those described above. In some implementations, one or more of the blocks may be implemented apart from other blocks, and by one or more different processors or devices. Further for explanatory purposes, the blocks of example method 700 are described as occurring in serial, or linearly. However, multiple blocks of example method 700 may occur in parallel. In addition, the blocks of example method 700 need not be performed in the order shown and/or one or more of the blocks of example method 700 need not be performed.

In the depicted example, a processor of a hanger receives from an infusion device a programmed flow rate pertaining to a fluid infusion provided by the infusion device (702). The processor determines, at a first time, using a weight sensor communicably connected to the processor and the infusion device, a first weight of an infusion container associated with the fluid infusion provided by the infusion device (704). The processor determines, at a second time, using the weight sensor, a second weight of the infusion container (706). The processor determines, based on the first weight and the second weight, a determined flow rate of the fluid infusion provided by the infusion device between the first time and the second time (708). The processor determines, a difference between the determined flow rate and the programmed flow rate (710). When a magnitude of the difference between the determined flow rate and the programmed flow rate satisfies a predetermined threshold, by the processor causes an output of the infusion device or the weight sensor to indicate the fault condition; and modifies an operation parameter of the infusion device to reduce the difference between the determined flow rate and the programmed flow rate (712).

In some implementations, the following detection criteria is used to identify flow rate accuracy errors. A fault condition exists when a cumulative flow rate deviates by more than ±20% from the programmed flow rate, and a critical volume of greater than 0.60 mL.

Repeated weight measurements are taken at intervals and a number of measurements are averaged to provide a running average over the time interval spanning the number of measurements (used in the average). For example, weight measures are taken at intervals of 100 milliseconds, and a series of 10 measurements are averaged to provide a running average for each 1 sec interval.

In some implementations, the system records the volume measured in 10 second intervals. The instantaneous flow rate is determined for an observation window of 20 seconds. The cumulative flowrate is calculated as the running average of instantaneous flow rate values from the start of the infusion. The system compares the previous volume measured (10 seconds earlier) to the current volume. If the difference is greater than the critical value, the hanger sends a signal to the PCU to alarm. In some implementations, the PCU includes closed loop infusion control capabilities and modifies one or more operation parameters of the infusion pump based on the signal received from the hanger 300 to correct a fault condition detected by the hanger 300.

The system then compares the cumulative flow rate to the programmed rate, deviations greater than 20% may generate a signal the causes the PCU to alarm. Pumps with nonconforming mechanism are typically detected sooner. For example a pump that is programmed to infuse at a rate of 0.1 mL/hr but is actually experiencing excessive flow greater than 5 mL/hr may be detected in less than 20 minutes.

In some implementations, a secondary bag is infused first after which a primary bag infuses. Two hangers can be used to monitor each container. The flow rate would be monitored on the secondary bag by a first hanger. Once completed, the second hanger would monitor the flow rate on the primary bag. Mixing of the fluids between the primary bag and the secondary bag is controlled by the height of the secondary bag in relation to the primary. Generally, no mixing is desired. However, differences in height, or pump pressure fluctuations can allow sympathetic flow (mixing) of the two fluids. The system may be used to monitor the fluid volumes in each bag and alert the user if the mixing exceeds 5% from the primary bag. The system may also alert the user of excessive sympathetic flow or when the secondary bag is emptied. In other words, the system may also maintain a record of the infusion.

Vibrations can affect the accuracy of the weight measurements. Flow rates in the operating range of 0.1 to 999 ml/hr produce flowrate pumping signal frequency of between 0.2 mHz to 1.7 Hz. When parasitic environmental vibrations occur in the same frequency range as the pumping signal frequency, filtering of the measurement signals may not adequately condition the signal. Other ways to reduce the impact of vibration includes vibration isolation by providing a mounting structure of weigh sensor with elastic and dampening elements to minimize the transfer of vibrations to the sensor. In some implementations, an accelerometer can be incorporated into the hanger 300 to help detect and remove vibrational noise. The accelerometer can measure movements and link the movements to parts of the signal that are corrupted by motion artifacts. The accelerometer can create a reference signal to allow removal of the motion noise.

In some implementations, the weighing system in the hanger 300 may be paused by the user while the pump, IV bag, or the patient is moved to prevent triggering nuisance alarms. The pause could be initiated by the user prior to moving, and limited for a certain time period after which the weighing sensor would restart automatically.

Figure 8A:
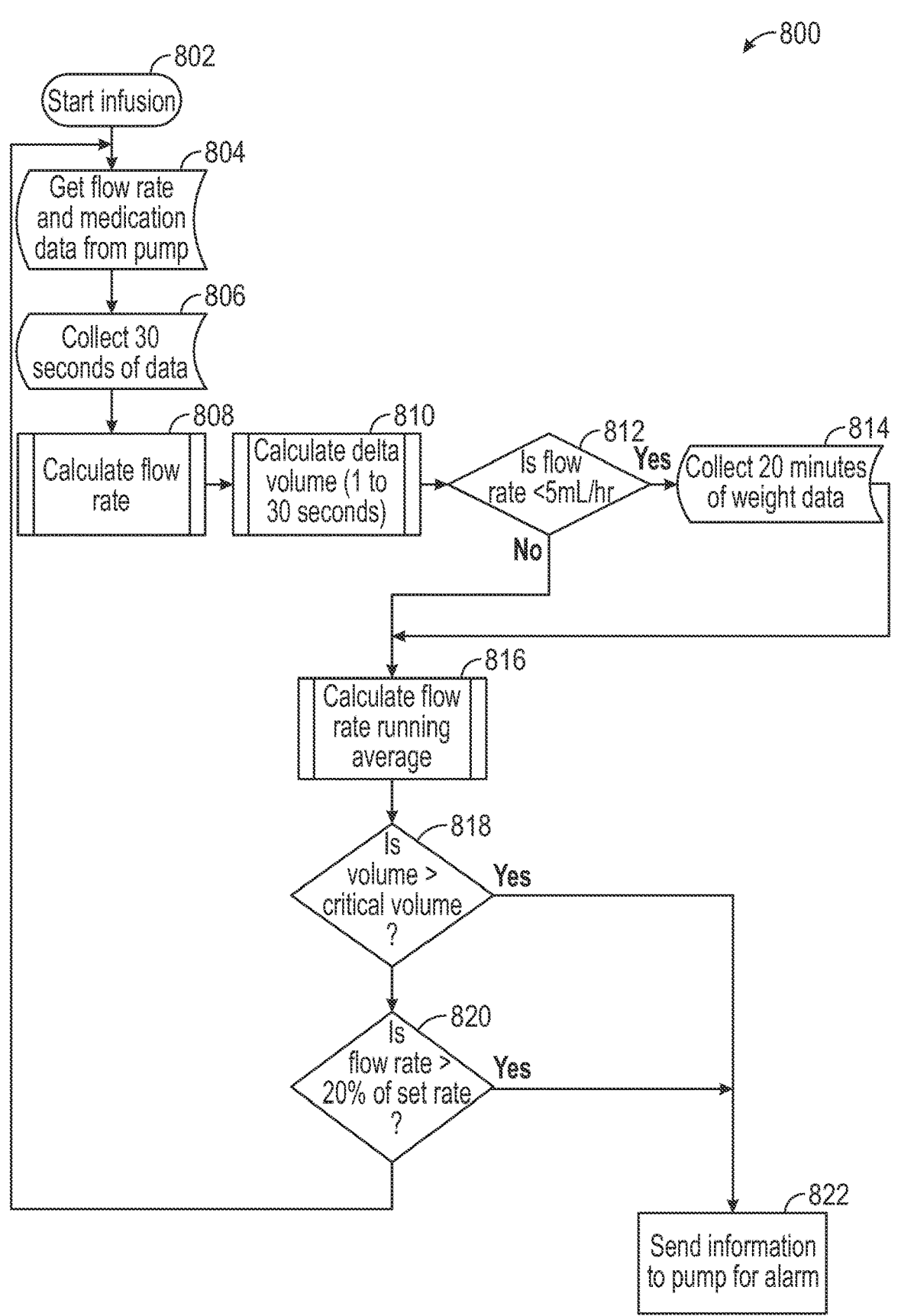
FIG. 8A depicts an example flow chart for determining a fault condition during an infusion process, according to aspects of the subject technology.

FIG. 8A depicts an example flow chart for determining a fault condition during an infusion process, according to aspects of the subject technology. The one or more of the blocks of method 800 may be implemented, for example, by one or more computing devices such as those described above. At a step 802, the infusion process is started. The controller of the infusion device causes a hanger 300 (e.g., in FIG. 3) to receive flow rate and medication data from the infusion pump at a step 804. A microprocessor in the hanger 300 causes the hanger 300 to collect weight data in a step 806. In some implementations, 30 seconds of weight data is collected at the step 806. The microprocessor in the hanger 300 calculates a flow rate based on a density of the fluid in the infusion container and the weight data in a step 808. The microprocessor in the hanger 300 calculates a change in volume between the current volume (at a current time) and a volume from an earlier time in a step 810. In some implementations, the earlier time is between 1 to 30 seconds prior to the current time. The microprocessor determines if the flow rate is less than a threshold flow rate in a step 812. In some implementations, the threshold flow rate is 5 ml/hour. In response to a determination at the step 812 that the flow rate is less than the threshold flow rate, the microprocessor in the hanger 300 causes the hanger 300 to collect weight data for an additional duration in a step 814. In some implementations, the additional duration is twenty minutes.

After either the additional weight data is collected in the step 814, or in response to a determination at the step 812 that the flow rate is greater than the threshold flow rate, the microprocessor causes the hanger 300 to calculate a running average of the flow rate in a step 816. The running average of the flow rate in the step 816 is calculated based, in part, on the flow rate calculated in the step 808. The running average of the flow rate is equivalent to the cumulative flow rate, and is calculated as the running average of instantaneous flow rate values from the start of the infusion.

At a step 818, the microprocessor of the hanger 300 determines if a volume measured at a previous time differs from a current volume by an amount greater than a critical value. In some implementations, the previous volume is measured 10 seconds earlier, and the critical value of 0.6 ml. The determination at the step 818 is based, in part, on the change in volume calculated at the step 810. If the difference is greater than the critical value, the hanger 300 sends a signal to the infusion device (PCU) to sound or display an alarm, at a step 822.

Otherwise, if the difference in volume is less than the critical value, the microprocessor in the hanger 300 determines, at a step 820, if the cumulative flow rate deviates from the programmed rate by a threshold amount. In some implementations, the threshold amount is 20%. If the difference is greater than the threshold amount, the hanger 300 generates and sends a signal to the infusion device to sound or display an alarm, at the step 822.

Figure 8B:
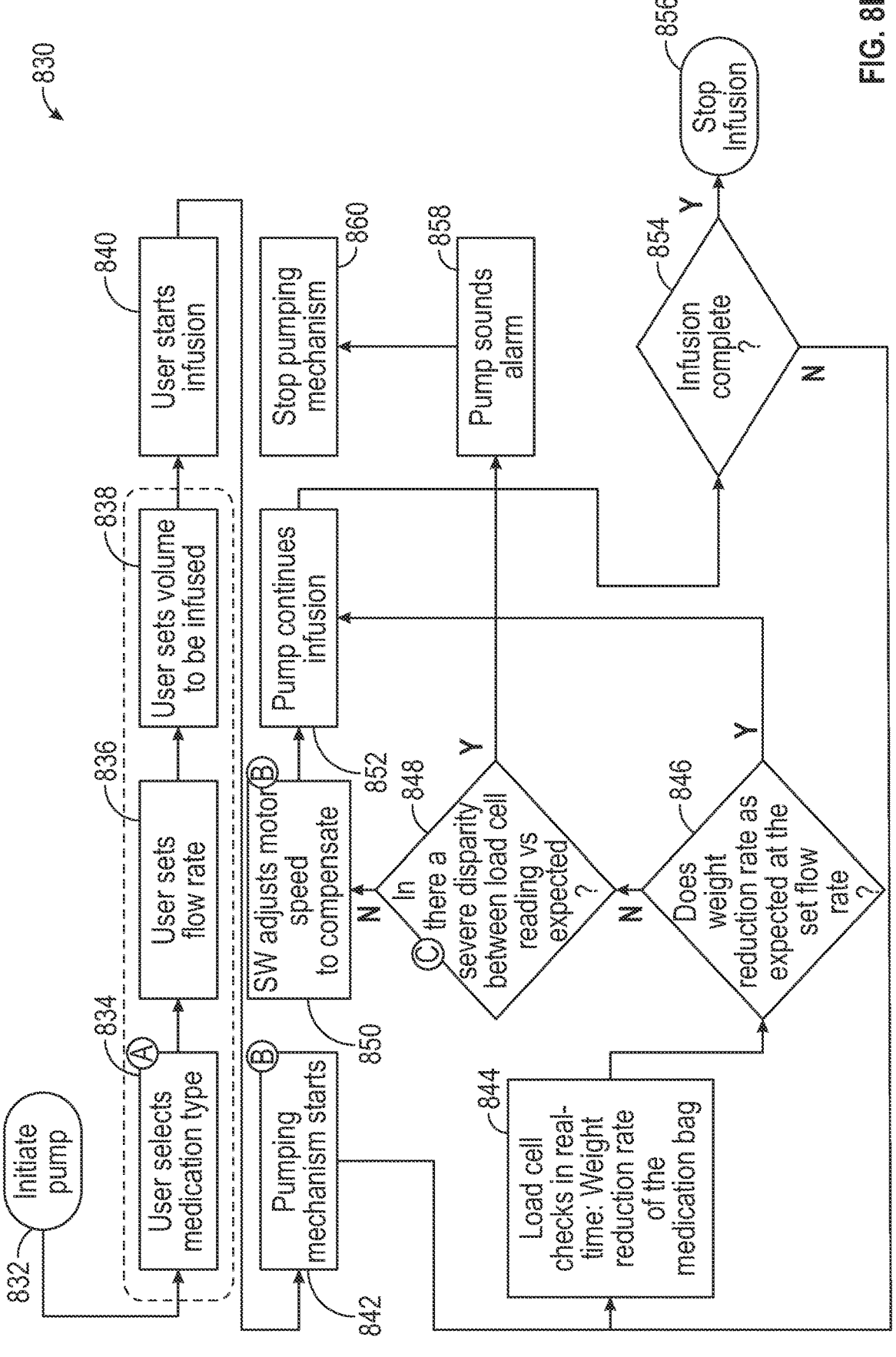
FIG. 8B depicts an example flow chart for determining a fault condition during an infusion process, according to aspects of the subject technology.

FIG. 8B depicts an example flow chart for determining a fault condition during an infusion process, according to aspects of the subject technology. The one or more of the blocks of method 830 may be implemented, for example, by one or more computing devices such as those described above. At a step 832, the infusion pump is initiated. A user selects, at a step 834 (or step A), a medication type of the medication to be infused. In the step 832, the infusion pump receives or retrieves data about densities of the medication types stored in its database (via internal memory or external memory attached to it). The load cell (e.g., the shear load cell 334) measures weight, and volume infused can be calculated using the formula: volume=mass/density.

At a step 836, the user sets a flow rate of the infusion process, and at a step 838, the user sets a volume to be infused (VTBI). In some implementations, the steps 834, 836, and 838 are replaced by an auto-population of the medication type, flow rate, and VTBI, by using a barcode reader to scan a barcode on the medication bag (e.g., IV bag) containing the medication to be infused.

At a step 840, the user starts the infusion process. The pumping mechanism starts at a step 842 (a first portion of a step B). Motor speeds of the pump mechanism may be pre-determined at their corresponding infusion flow rates. The infusion pump can include software that allows adjustment of the motor speed to be faster or slower than the pre-determined speed if there is a mismatch between (i) an actual volume infused at a given time and (ii) an expected volume infused at the given time.

A load cell (e.g., the shear load cell 334 in FIG. 3C) checks, in real-time, whether a weight reduction of the medication bag is consistent with an expected weight reduction from the expected infusion flow rate. At a step 846, in accordance with a determination that the weight reduction rate is as expected at the set flow rate, the infusion pump continues infusion at a step 852. In accordance with a determination at a step 854 that the infusion process is completed, the infusion is stopped at a step 856. In accordance with a determination at the step 854 that the infusion process is not yet completed, the infusion continues while real-time monitoring of the weight reduction rate resumes at the step 844.

In accordance with a determination, at the step 846, that the weight reduction rate is not as expected at the set flow rate, a determination is made at the step 848 (or a step C) whether there is a severe disparity between the measurements from the load cell and the expected weight reduction. The specifications of a range of acceptable differences, and an impermissible "severe" disparity, between an actual infused volume, and an expected volume infused may be set by the manufacturer of the infusion pump. The step 848 (or step C) provides added security to ensure that any gross inaccuracies are detected early and potential harm to patients may be avoided.

The infusion pump sounds an alarm at a step 858 if there is a severe disparity and the pumping mechanism is stopped at a step 860. If there is not a severe disparity between the measurements from the load cell and the expected weight reduction, software in the infusion pump causes, at a step 850 (or a second portion of the step B), a motor speed to be adjusted to compensate for deviations from the expected weight reduction (e.g., there is a mismatch between (i) an actual infused volume a given time, and (ii) an expected volume infused at the given time). For example, the motor speed may be decreased if there is over-infusion. The motor speed may be increased if an under-infusion is detected. The infusion pump continues the infusion process at the step 852, until infusion is completed (at the step 856), or until a fault stops the pumping mechanism (at the step 860).

FIG. 9 tabulates some example testing data from an example system implemented according to aspects of the subject technology. The table list the measurements made with the IV bag hanger load cell compared, to the results measured on the downstream side with a laboratory scale. The tests were run for a period of one hour. The highlighted cells show the results that exceeded the 20% detection criteria for both. The final column list the results from the IV bag detection criteria compared to the downstream scale, a zero indicates that the IV bag detected the fault, or is in agreement with the results of the downstream scale. A "1" would indicate a type 1 error where the IV bag hanger load cell did not detect a failure, and a "2" indicates a type 2 error where the IV bag would have caused an alarm since the flow rate error is greater than 20%. The results show that there were no type 1 errors, there were four type 2 errors which occurred at the lower flow rates. Type 1 errors determine the suitability of the measurement system. The lack of any Type 1 errors indicate that the hanger 300 is capable in this respect. Type 2 errors cause false alarms that prompt a clinician to evaluate the alarm to make sure that there were no issues.

Observation periods longer than the testing period of 1 hour, would likely result in upstream results that more closely match the downstream flow rate, particularly for the 1 mL/hr rate. The hanger system demonstrates its ability to detect faults, but with the possibility that some nuisance alarms may also occur.

The hanger 300 may be used with any infusion pump and provide some of the guardrails, monitoring, alerting, and connectivity features. For example, the hanger 300 can be used with any pump provided that flow rate information is provided to the hanger 300 either by direct communication to the pump, or via interoperability with a hospital network. The hanger 300 can also be used alone for gravity infusions to provide these features. The Bluetooth communication circuitry inside the hanger 300 can also provide these features to a user (e.g., care provider or the patient) with a tablet or mobile phone application.

In some implementations, a method of detecting a fault condition in an infusion process includes receiving, by a processor, from an infusion device, a programmed flow rate pertaining to a fluid infusion provided by the infusion device. The method includes determining, by the processor, at a first time, using a weight sensor communicably connected to the processor and the infusion device, a first weight of an infusion container associated with the fluid infusion provided by the infusion device. The method includes determining, by the processor, at a second time, using the weight sensor, a second weight of the infusion container. The method includes determining, by the processor, based on the first weight and the second weight, a determined flow rate of the fluid infusion provided by the infusion device between the first time and the second time. The method includes determining, by the processor, a difference between the determined flow rate and the programmed flow rate. When a magnitude of the difference between the determined flow rate and the programmed flow rate satisfies a predetermined threshold, causing an output of the infusion device or the weight sensor to indicate the fault condition; and modifying an operation parameter of the infusion device to reduce the difference between the determined flow rate and the programmed flow rate.

In some implementations, the determined flow rate includes a cumulative flow rate derived from an average of instantaneous flow rate values measured from a start of the fluid infusion. In some implementations, the method further includes obtaining a density of a fluid in the infusion container; determining a volume of the fluid delivered by the infusion device during the fluid infusion based on the density of the fluid in the infusion container, the first weight, and the second weight. The method includes determining if the volume of the fluid exceeds a critical volume, and determining whether the volume of the fluid exceeds the critical volume. When the volume of the fluid exceeds the critical volume, causing, by the processor, the output of the infusion device to indicate the fault condition.

In some implementations, the fault condition includes an over-infusion, and the predetermined threshold is met when the determined flow rate is higher than the programmed flow rate by more than 20%. In some implementations, the method further includes infusing, by the infusion device, a second fluid from a secondary infusion container. The secondary infusion container is connected to a second weight sensor; and monitoring, using the second weight sensor, a sympathetic flow between the secondary infusion container and the infusion container. The processor causes the output of the infusion device or the weight sensor to indicate the fault condition when the sympathetic flow causes a mixing of more than a threshold percentage of fluid from the infusion container into a flow of the second fluid from the secondary infusion container.

In some implementations, the infusion device includes an infusion pump configured to receive fluid from the infusion container during a fill phase, the method further includes: infusing the fluid from the infusion pump to a patient during a delivery phase. Calculating the determined flow rate includes using linear regression to determine an average flow rate for both the fill phase and the delivery phase.

In some implementations, a cam cycle of the infusion device includes a fill phase and a delivery phase, and the average flow rate is determined, by the processor, based on weight data collected, by the weight sensor, during at least five cam cycles.

In some implementations, the infusion device further includes a compensating finger that is configured to deliver some flow to the patient during the fill phase.

In some implementations, the weight sensor further includes non-volatile random-access memory (nvSRAM) configured to store calibration values, flow rates, and/or measured weight data.

In some implementations, the infusion device is configured to transfer information recorded at the weight sensor to an internal network of a care facility for coordination with an additional system at the care facility.

In some implementations, detecting the fault condition further includes determining a presence of a leaking occluder finger or broken mechanism frame bosses in the infusion device, based on weight data measured by the weight sensor.

In some implementations, detecting the fault condition occurs when the infusion device is turned off and no warning signal is issued from the infusion device. In some implementations, an indication of a presence of the fault condition is provided at the output of the weight sensor.

In some implementations, the method further includes isolating the weight sensor from vibrations in a surrounding of the weight sensor. In some implementations, isolating the weight sensor from vibrations includes placing an elastomer isolator between a housing enclosing the weight sensor, and the weight sensor.

In some implementations, the method further includes recording additional weight data for a first time duration, prior to determining the difference between the determined flow rate and the programmed flow rate, when the programmed flow rate is below a threshold value. In some implementations, the threshold value is 5 ml/hour. In some implementations, the method further includes associating the weight sensor and the infusion container to a pump channel of the infusion device.

In some implementations, the weight sensor includes a shear load cell. In some implementations, the method further includes detecting a fault condition simultaneously in more than one infusion process.

In some implementations, a smart pole includes a pole cap supporting a weight sensor connected to an infusion container, the weight sensor configured to measure a weight of the infusion container associated with a fluid infusion provided by an infusion device. The smart pole includes an actuator, configured to adjust a height of the smart pole to change a height of the infusion container, and a processor configured to: receive a flow rate programmed into the infusion device and pertaining to the fluid infusion provided by the infusion device; determine, at a first time during the fluid infusion, using the weight sensor communicably connected to the processor and the infusion device, a first weight of the infusion container; determine, at a second time during the fluid infusion, using the weight sensor, a second weight of the infusion container; determine a flow rate of the fluid infusion between the first time and the second time based on the first weight and the second weight; determine a difference between the determined flow rate and the programmed flow rate; and send instructions to the actuator to change the height of the smart pole when a magnitude of the difference between the determined flow rate and the programmed flow rate satisfies a predetermined threshold.

In some implementations, the actuator causes the smart pole to have a greater height when the determined flow rate is lower than the programmed flow rate, and a magnitude of the difference satisfies the predetermined threshold. In some implementations, the actuator causes the smart pole to have a lower height when the determined flow rate is higher than the programmed flow rate, and a magnitude of the difference satisfies the predetermined threshold. In some implementations, the pole cap supports a plurality of weight sensors, each connected to a respective infusion container.

Figure 10:
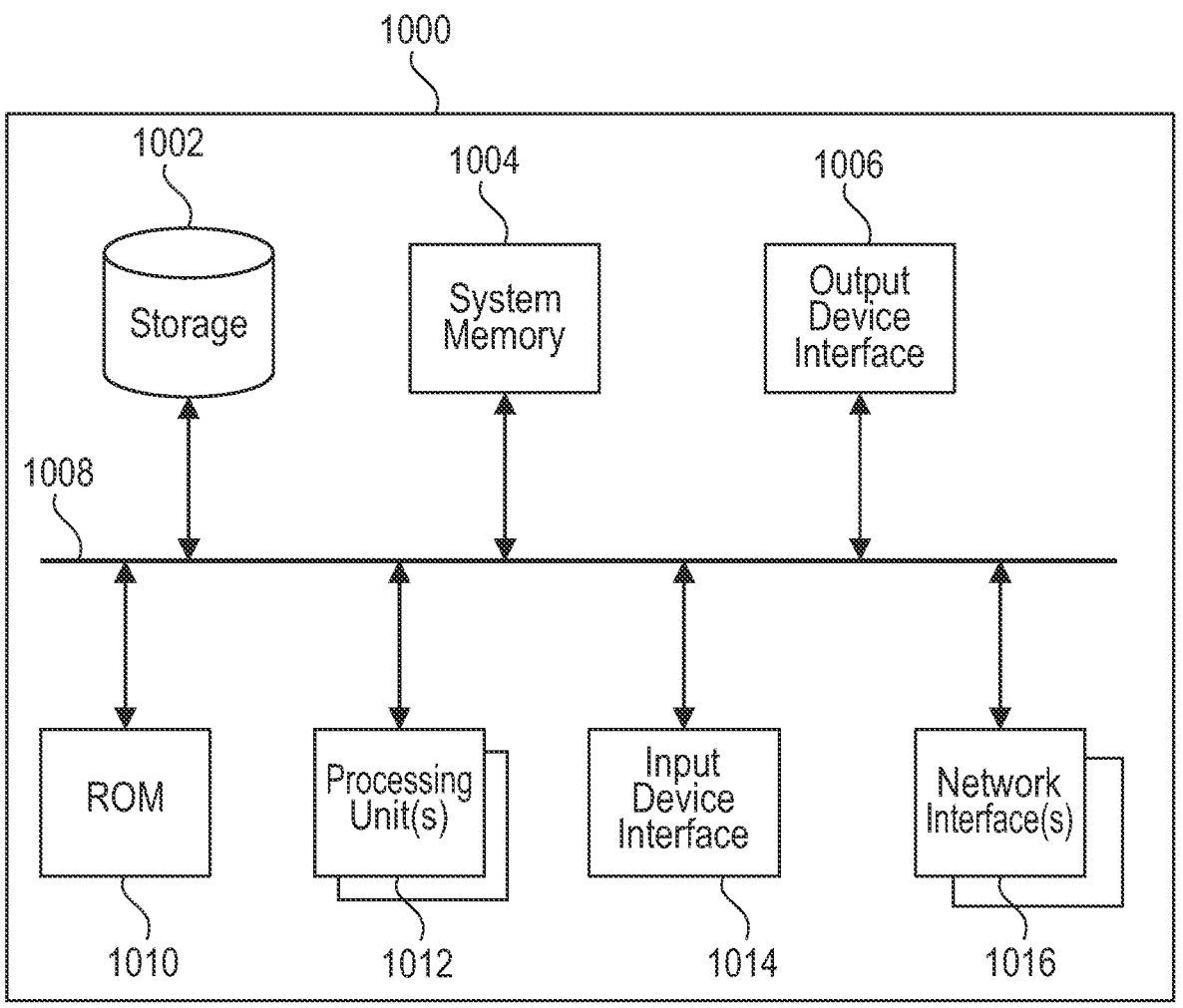
FIG. 10 is a conceptual diagram illustrating an example electronic system for determining a fault condition during an infusion process, according to aspects of the subject technology.

FIG. 10 is a conceptual diagram illustrating an example electronic system for determining a fault condition during an infusion process, according to aspects of the subject technology. Electronic system 1000 may be a computing device for execution of software associated with one or more portions or steps of process 1000, or components and processes provided by FIGS. 1-9, including but not limited to server 130, computing hardware within patient care device 12, or terminal device 132. Electronic system 1000 may be representative, in combination with the disclosure regarding FIGS. 1-9. In this regard, electronic system 1000 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 1000 may include various types of computer readable media and interfaces for various other types of computer readable media. In the depicted example, electronic system 1000 includes a bus 1008, processing unit(s) 1012, a system memory 1004, a read-only memory (ROM) 1010, a permanent storage device 1002, an input device interface 1014, an output device interface 1006, and one or more network interfaces 1016. In some implementations, electronic system 1000 may include or be integrated with other computing devices or circuitry for operation of the various components and processes previously described.

Bus 1008 collectively represents all system, peripheral, and chipset buses that communicatively connect the numerous internal devices of electronic system 1000. For instance, bus 1008 communicatively connects processing unit(s) 1012 with ROM 1010, system memory 1004, and permanent storage device 1002.

From these various memory units, processing unit(s) 1012 retrieves instructions to execute and data to process in order to execute the processes of the subject disclosure. The processing unit(s) can be a single processor or a multi-core processor in different implementations.

ROM 1010 stores static data and instructions that are needed by processing unit(s) 512 and other modules of the electronic system. Permanent storage device 1002, on the other hand, is a read-and-write memory device. This device is a non-volatile memory unit that stores instructions and data even when electronic system 1000 is off. Some implementations of the subject disclosure use a mass-storage device (such as a magnetic or optical disk and its corresponding disk drive) as permanent storage device 1002.

Other implementations use a removable storage device (such as a floppy disk, flash drive, and its corresponding disk drive) as permanent storage device 1002. Like permanent storage device 1002, system memory 1004 is a read-and-write memory device. However, unlike storage device 1002, system memory 1004 is a volatile read-and-write memory, such a random access memory. System memory 1004 stores some of the instructions and data that the processor needs at runtime. In some implementations, the processes of the subject disclosure are stored in system memory 1004, permanent storage device 1002, and/or ROM 1010. From these various memory units, processing unit(s) 1012 retrieves instructions to execute and data to process in order to execute the processes of some implementations.

Bus 1008 also connects to input and output device interfaces 1014 and 1006. Input device interface 1014 enables the user to communicate information and select commands to the electronic system. Input devices used with input device interface 1014 include, e.g., alphanumeric keyboards and pointing devices (also called "cursor control devices"). Output device interfaces 1006 enables, e.g., the display of images generated by the electronic system 1000. Output devices used with output device interface 1006 include, e.g., printers and display devices, such as cathode ray tubes (CRT) or liquid crystal displays (LCD). Some implementations include devices such as a touchscreen that functions as both input and output devices.

Also, as shown in FIG. 10, bus 1008 also couples electronic system 1000 to a network (not shown) through network interfaces 1016. Network interfaces 1016 may include, e.g., a wireless access point (e.g., Bluetooth or WiFi) or radio circuitry (e.g., transceiver, antenna, amplifier) for connecting to a wireless access point. Network interfaces 1016 may also include hardware (e.g., Ethernet hardware) for connecting the computer to a part of a network of computers such as a local area network ("LAN"), a wide area network ("WAN"), wireless LAN, personal area network ("PAN"), or an Intranet, or a network of networks, such as the Internet. Any or all components of electronic system 1000 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices specifically configured for the infusion features described can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a specifically configured computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all implementations, or one or more implementations. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some embodiments, include a signal utilized to transmit one or more representations of the information. While recited in the singular, it will be understood that a message may be composed, transmitted, stored, received, etc. in multiple parts.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or cellular networks.

What is claimed is:

1. A method of detecting a fault condition in an infusion process, the method comprising:

receiving, by a processor, a flow rate programmed into an infusion device and pertaining to a fluid infusion provided by the infusion device;

determining, by the processor, at a first time, using a weight sensor communicably connected to the processor and the infusion device, a first weight of an infusion container associated with the fluid infusion provided by the infusion device;

determining, by the processor, at a second time during the fluid infusion, using the weight sensor, a second weight of the infusion container;

determining, by the processor, an actual volume of the fluid infusion provided by the infusion device between the first time and the second time based on the first weight and the second weight;

determining, by the processor, a difference between the determined actual volume and an expected volume for the programmed flow rate;

determine an occurrence of an under-infusion or an over-infusion based on the determined difference;

when a magnitude of the difference satisfies a predetermined threshold for a fault condition, by the processor:

causing an output of the infusion device or the weight sensor to indicate the fault condition;

automatically receiving height information indicating a height of the infusion container;

determining, based on the height information, that the occurrence of the under-infusion or the over-infusion can be corrected based on adjusting the height of the infusion container or a motor speed of the infusion device; and automatically sending, based on determining that the occurrence can be corrected based on adjusting the height of the infusion container or a motor speed of the infusion device, a signal to a structure supporting the infusion container to adjust the height of the infusion container, to reduce the difference and correct the under-infusion or the over-infusion, wherein when an under-infusion is determined, the height is increased to increase the flow rate to correct the under-infusion, and when an over-infusion is determined, the height is decreased to correct the over-infusion.

2. The method of claim 1, further comprising:

recording respective volumes at predetermined intervals;

determining instantaneous flow rate values over respective observation windows of time;

determining a cumulative flow rate from an average of the instantaneous flow rate values measured from a start of the fluid infusion;

comparing a prior recorded volume to a current volume; and sending the signal when, based on the comparing, a difference between the prior recorded volume and the current volume is greater than a critical value.

3. The method of claim 1, further comprising:

obtaining a density of a fluid in the infusion container;

determining a volume of the fluid delivered by the infusion device during the fluid infusion based on the density of the fluid in the infusion container, the first weight, and the second weight;

determining if the volume of the fluid exceeds a critical volume, determining whether the volume of the fluid exceeds the critical volume; and when the volume of the fluid exceeds the critical volume, causing, by the processor, the output of the infusion device to indicate the fault condition.

4. The method of claim 1, wherein the fault condition comprises an over-infusion, and the predetermined threshold is met when the determined actual volume of the fluid infusion is higher than the expected volume by more than 20%.

5. The method of claim 1, further comprising:

infusing, by the infusion device, a second fluid from a secondary infusion container, wherein the secondary infusion container is connected to a second weight sensor; and monitoring, using the second weight sensor, a sympathetic flow between the secondary infusion container and the infusion container, wherein the processor causes the output of the infusion device or the weight sensor to indicate the fault condition when the sympathetic flow causes a mixing of more than a threshold percentage of fluid from the infusion container into a flow of the second fluid from the secondary infusion container.

6. The method of claim 1, wherein the infusion device comprises an infusion pump configured to receive fluid from the infusion container during a fill phase, the method further includes:

infusing the fluid from the infusion pump to a patient during a delivery phase; and measuring a first drop in volume of the fluid in the infusion container during the fill phase;

measuring a second drop in the volume of the fluid in the infusion container during the delivery phase;

determining an average flow rate for both the fill phase and the delivery phase using linear regression of a best fit of the measured first drop and the measured second drop.

7. The method of claim 6, wherein the average flow rate is determined for a predetermined number of cam cycles of the infusion device based on weight data collected, by the weight sensor, during the predetermined number of cam cycles.

8. The method of claim 7, wherein the infusion device further includes a compensating finger that is configured to deliver some flow to the patient during the fill phase.

9. The method of claim 1, wherein the weight sensor further includes non-volatile random-access memory (nvSRAM) configured to store calibration values, flow rates, and/or measured weight data.

10. The method of claim 1, wherein the infusion device is configured to transfer information recorded at the weight sensor to an internal network of a care facility for coordination with an additional system at the care facility.

11. The method of claim 1, wherein detecting the fault condition further includes determining a presence of a leaking occluder finger or broken mechanism frame bosses in the infusion device, based on weight data measured by the weight sensor.

12. The method of claim 1, further comprising isolating the weight sensor from vibrations in a surrounding of the weight sensor.

13. The method of claim 12, wherein isolating the weight sensor from vibrations includes placing an elastomer isolator between a housing enclosing the weight sensor, and the weight sensor.

14. The method of claim 1, further comprising recording additional weight data for a first time duration, prior to determining the difference between the determined actual volume and the expected volume, when the programmed flow rate is below a threshold value.

15. The method of claim 1, wherein the weight sensor comprises a shear load cell.

16. The method of claim 1, further comprising detecting a fault condition simultaneously in more than one infusion process.

17. The method of claim 1, further comprising, when the magnitude of the difference satisfies the predetermined threshold for the fault condition, by the processor:

determining that the occurrence can be corrected based on adjusting the height of the infusion container or a motor speed of the infusion device; and automatically causing an adjustment to the motor speed of the infusion device in combination with sending the signal to adjust the height of the infusion device, to reduce the difference and correct the under-infusion or the over-infusion.

*     *     *     *     *